United States Patent
Tsang et al.

(10) Patent No.: US 9,527,957 B2
(45) Date of Patent: Dec. 27, 2016

(54) HIGH GLASS TRANSITION TEMPERATURE PHOTOIMAGEABLE POLYCARBONATE POLYMERS WITH PENDENT POLYCYCLIC FUNCTIONAL GROUPS

(71) Applicant: PROMERUS, LLC, Brecksville, OH (US)

(72) Inventors: W. C. Peter Tsang, Brecksville, OH (US); Andrew Bell, Brecksville, OH (US); Keitaro Seto, Brecksville, OH (US)

(73) Assignee: PROMERUS, LLC, Brecksville, OH (US)

( * ) Notice: Subject to any disclaimer, the term of this patent is extended or adjusted under 35 U.S.C. 154(b) by 0 days.

(21) Appl. No.: 14/759,708

(22) PCT Filed: Feb. 28, 2014

(86) PCT No.: PCT/US2014/019192
§ 371 (c)(1),
(2) Date: Jul. 8, 2015

(87) PCT Pub. No.: WO2014/134373
PCT Pub. Date: Sep. 4, 2014

(65) Prior Publication Data
US 2015/0353679 A1 Dec. 10, 2015

Related U.S. Application Data

(60) Provisional application No. 61/770,844, filed on Feb. 28, 2013, provisional application No. 61/846,495, filed on Jul. 15, 2013.

(51) Int. Cl.
*C08F 2/46* (2006.01)
*C08F 2/50* (2006.01)
*C08G 61/04* (2006.01)
*C08G 64/06* (2006.01)
*C09D 169/00* (2006.01)
*C07D 303/04* (2006.01)
*C08G 64/34* (2006.01)
*G03F 7/004* (2006.01)
*G03F 7/039* (2006.01)

(52) U.S. Cl.
CPC ............. *C08G 64/06* (2013.01); *C07D 303/04* (2013.01); *C08G 64/34* (2013.01); *C09D 169/00* (2013.01); *G03F 7/0045* (2013.01); *G03F 7/0392* (2013.01)

(58) Field of Classification Search
CPC ....... C08G 64/06; C08G 64/34; C07D 303/04; C09D 169/00; G03F 7/0392; G03F 7/0045
USPC ............................. 522/71, 189, 184, 1; 520/1
See application file for complete search history.

(56) References Cited

U.S. PATENT DOCUMENTS

2012/0031556 A1* 2/2012 Bell ...................... B23K 35/26
156/307.3

FOREIGN PATENT DOCUMENTS

EP 0453275 * 10/1991
JP 60-079038 A 5/1985

OTHER PUBLICATIONS

Adrien Clinet, et al., "Synthesis and Odour Evaluation of Alcohols Bearing a cis-1,2-dimethyl Norbornane Moiety," Flavour and Fragrance Journal, vol. 28, pp. 53-61 (2013).
Chemical Abstracts Service, "Heat-resistant polyesters," Database Accession No. 1985:506213.

* cited by examiner

*Primary Examiner* — Ling Choi
*Assistant Examiner* — Jessica E Whiteley
(74) *Attorney, Agent, or Firm* — Balaram Gupta

(57) ABSTRACT

Embodiments in accordance with the present invention relate generally to polycarbonate polymers having repeat units derived from polycyclic-epoxide monomers and methods of using such polymers and compositions containing them, and more specifically to polymers and compositions of polycarbonates that encompass repeat units derived from norbornane and tetracyclododecane, and methods of using such compositions.

24 Claims, No Drawings

HIGH GLASS TRANSITION TEMPERATURE PHOTOIMAGEABLE POLYCARBONATE POLYMERS WITH PENDENT POLYCYCLIC FUNCTIONAL GROUPS

CROSS REFERENCE TO RELATED APPLICATIONS

This application is a national phase application of PCT Application No. PCT/US2014/019192 filed Feb. 28, 2014, and published as International Publication No. WO 2014/134373 A1 on Sep. 4, 2014, and which claims the benefit of U.S. Provisional Application No. 61/770,844, filed Feb. 28, 2013 and the benefit of U.S. Provisional Application No. 61/846,495, filed Jul. 15, 2013, all of which are incorporated herein by reference in their entirety.

TECHNICAL FIELD

Embodiments in accordance with the present invention relate generally to polycarbonate polymers having repeat units derived from polycyclic epoxide monomers and methods of using such polymers and compositions containing them, and more specifically to polymers and compositions of polycarbonates that encompass repeat units derived from norbornane and tetracyclododecane, and methods of using such compositions.

BACKGROUND

Optically clear commercial poly(alkylene carbonate) binder materials, such as poly(ethylene carbonate) (PEC) and poly(propylene carbonate) (PPC), have demonstrated utility in air-gap formation for electrical/optical interconnects, microelectromechanical systems (MEMS) device fabrication, microfluidics, and micro-reactor applications because of their photoimageability in the presence of a photoactive additive. For example, Unity® 2203P, which contains a poly(alkylene carbonate), can be patterned by UV exposure (typically at 365 nm) in the presence of a suitable additive. However, retention of pattern fidelity and feature resolution is limited due to polymer flow issues (e.g., rounded features, slanting side walls) in post-exposure development. These thermal flow properties are attributed to the low glass transition temperature ($T_g$, 40° C.) of the base polymer (PPC) which is significantly lower than the development temperature. Thus, there is a need to develop new photoimageable polymers which are formed from readily available monomers and exhibit the following properties: (i) high $T_g$ ($T_g \geq 80°$ C.), (ii) soluble in common process solvents, (iii) have sufficient $M_w$ (at least 15,000) to attain formulation viscosity required for thin film generation by spin or spray coating and have mechanical strength, (iv) decompose cleanly at low temperatures (<200° C.) in the presence of a photoactive additive, and (v) leave essentially no residue after post-exposure thermal development. The low residue requirement is important in cases where cleaning is not possible, e.g., encapsulated microchannels generated from decomposition of sacrificial materials covered by an overcoat.

U.S. Pat. No. 6,743,570 B2 ('570 patent) discloses a method of using heat-depolymerizable polycarbonate, such as poly(cyclohexene carbonate) to create a nano-fluidic device. In this method, areas of polycarbonate exposed to e-beam were removed by immersion in isopropanol, with optional plasma cleaning in a UV-ozone cleaner. In a later part of the device fabrication, after depositing a capping layer, the underlying heat-depolymerizable polycarbonate was removed by baking at temperatures above 300° C. for 30 min or longer. No photoactive component was mentioned in the disclosure. The poly(cyclohexene carbonate) was prepared from alternating copolymerization of cyclohexene oxide with carbon dioxide using (BDI)ZnOR (R=Ac, Me) catalysts in accordance with the procedures described by Cheng et al., J. Am. Chem. Soc. 1998, 120, 11018-11019; also see J. Am. Chem. Soc. 2003, 125, 11911-11924. Various other catalyst systems have also been used for the preparation of polycarbonates by alternating copolymerization of epoxide with carbon dioxide, see Catal. Sci. Technol. 2012, 2, 2169-2187 and references cited therein.

It should be noted that the post e-beam immersion in isopropanol processing as disclosed in '570 patent may not be suitable in many applications where the polycarbonate is intended for removal after an overmolding step, such as in a typical semiconductor fabrication. Furthermore, the alternative harsh baking conditions (higher than 300° C. for a period in excess of 30 minutes) may not be compatible with expected throughput and thermally sensitive components in a semiconductor device.

U.S. Pat. No. 6,586,154 B1 ('154 patent) discloses a series of photoresist polymer compositions which are polycarbonates derived from various polycyclic diols and carbon dioxide. It should be noted that the disclosures of '154 patent appear to require a wet development step after a post-exposure bake, as disclosed therein several of the examples included a 40-second tetramethylammonium hydroxide (TMAH) development step.

U.S. Patent Application Publication No. 2004/0132855 discloses a series of photodefinable polymers, which include polynorbornenes, polycarbonates, polyethers and polyesters. As disclosed therein, residues formed from certain decomposable materials, such as polyimide, polynorbornene, and polycarbonate are removed by plasma reactive ion etch (RIE). This aspect of the process may not be suitable in cases where the microchannel is encapsulated by an overcoat.

Accordingly, there is still a need for developing polymer compositions that can be dry developed with essentially no residue left behind.

Other objects and further scope of the applicability of the present invention will become apparent from the detailed description that follows.

SUMMARY OF THE INVENTION

Surprisingly, it has now been found that polycyclic carbonates with a backbone similar to poly(propylene carbonate) (PPC) decompose by generation of low molecular weight cyclic products by chain scission and intramolecular back-biting. Specifically, replacing at least some of the methyl group in PPC with a rigid polycyclic substituent, such as norbornane or tetracyclododecane increases the glass transition temperature ($T_g$) of the polycarbonate without affecting the decomposition mechanism. The higher $T_g$ of these polymers should improve pattern fidelity by reducing polymer flow issues typically encountered during post-exposure thermal development. The polymer embodiments with pendant polycyclic moieties are generated by alternating copolymerization of carbon dioxide and the corresponding epoxide using a ligand-supported metal catalyst (e.g., cobalt, and zinc).

DETAILED DESCRIPTION OF THE INVENTION

The terms as used herein have the following meanings:

As used herein, the articles "a," "an," and "the" include plural referents unless otherwise expressly and unequivocally limited to one referent.

Since all numbers, values and/or expressions referring to quantities of ingredients, reaction conditions, etc., used herein and in the claims appended hereto, are subject to the various uncertainties of measurement encountered in obtaining such values, unless otherwise indicated, all are to be understood as modified in all instances by the term "about."

Where a numerical range is disclosed herein such range is continuous, inclusive of both the minimum and maximum values of the range as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub-ranges subsumed therein. For example, a stated range of from "1 to 10" should be considered to include any and all sub-ranges between the minimum value of 1 and the maximum value of 10. Exemplary sub-ranges of the range 1 to 10 include, but are not limited to, 1 to 6.1, 3.5 to 7.8, and 5.5 to 10, and so on so forth.

As used herein, "hydrocarbyl" refers to a moiety or a group that contains only carbon and hydrogen, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen. The term perhalocarbyl refers to a hydrocarbyl group where all of the hydrogens have been replaced by a halogen.

As used herein, the expression "$(C_1-C_6)$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$(C_1-C_4)$alkoxy", "$(C_1-C_4)$thioalkyl" "$(C_1-C_4)$alkoxy$(C_1-C_4)$alkyl", "hydroxy$(C_1-C_4)$alkyl", "$(C_1-C_4)$alkylcarbonyl", "$(C_1-C_4)$alkoxycarbonyl$(C_1-C_4)$alkyl", "$(C_1-C_4)$alkoxycarbonyl", "amino$(C_1-C_4)$alkyl", "$(C_1-C_4)$alkylamino", "$(C_1-C_4)$alkylcarbamoyl$(C_1-C_4)$alkyl", "$(C_1-C_4)$dialkylcarbamoyl$(C_1-C_4)$alkyl" "mono- or di-$(C_1-C_4)$alkylamino$(C_1-C_4)$alkyl", "amino$(C_1-C_4)$alkylcarbonyl" "diphenyl$(C_1-C_4)$alkyl", "phenyl$(C_1-C_4)$alkyl", "phenylcarboyl$(C_1-C_4)$alkyl" and "phenoxy$(C_1-C_4)$alkyl" are to be construed accordingly.

As used herein, the expression "cycloalkyl" includes all of the known cyclic groups, including polycyclic groups further defined below, such as bicycloalkyl, and so on. Representative examples of "cycloalkyl," which are monocyclic groups, include without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "bicycloalkyl" includes all of the known bicyclic groups. Representative examples of "$C_6-C_{12}$-bicycloalkyl" includes without any limitation bicyclo[2.1.1]hexane, bicyclo[2.2.1]heptane, bicyclo[3.2.1]octane, bicyclo[2.2.2]octane, bicyclo[3.2.2]nonane, bicyclo[3.3.]nonane, bicyclo[3.3.2]decane, bicyclo[4.3.1]decane, bicyclo[4.4.1]undecane, bicyclo[5.4.1]dodecane, and the like. Derived expressions such as "bicycloalkoxy", "bicycloalkylalkyl", "bicycloalkylaryl", "bicycloalkylcarbonyl" are to be construed accordingly.

As used herein, the expression "tricycloalkyl" includes all of the known tricyclic groups. Representative examples of "$C_7-C_{14}$-tricycloalkyl" includes without any limitation tricyclo[2.2.1.0$^{2,6}$]heptane, tricyclo[3.2.1.0$^{2,4}$]octane, tricyclo[4.2.1.0$^{2,5}$]nonane, octahydro-1H-4,7-methanondene, octahydro-1H-4,7-ethanoindene, octahydro-1H-cyclopropa[a]pentalene, decahydrocyclopenta[cd]-pentalene, dodecahydro-1H-phenalene, adamantyl and the like. Derived expressions such as "tricycloalkoxy", "tricycloalkylalkyl", "tricycloalkylaryl", "tricycloalkylcarbonyl" are to be construed accordingly.

As used herein, the expression "tetracycloalkyl" includes all of the known tetracyclic groups. Representative examples of "$C_{10}-C_{14}$-tetracycloalkyl" includes without any limitation tetracyclo[3.2.2.2$^{1,5}$.0$^{2,4}$]undecane, decahydro-1,4:5,8-dimethanonaphthalene and the like. Derived expressions such as "tetracycloalkoxy", "tetracycloalkylalkyl", "tetracycloalkylaryl", "tetracycloalkylcarbonyl" are to be construed accordingly.

As used herein, the expression "$(C_6-C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "$(C_6-C_{10})$arylsulfonyl," is to be construed accordingly.

As used herein, the expression "$(C_6-C_{10})$aryl$(C_1-C_4)$alkyl" means that the $(C_6-C_{10})$aryl as defined herein is further attached to $(C_1-C_4)$alkyl as defined herein. Representative examples include benzyl, phenylethyl, 2-phenylpropyl, 1-naphthylmethyl, 2-naphthylmethyl and the like.

As used herein, the expression "heteroaryl" includes all of the known heteroatom containing aromatic radicals. Representative 5-membered heteroaryl radicals include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2H$, an ester, an amide, $C_1$-$C_6$alkoxy, $C_1$-$C_6$thioalkyl, $C_1$-$C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

As used herein, the symbol "〜" denotes a position at which the bonding takes place with another repeat unit or another atom or molecule or group or moiety as appropriate with the structure of the group as shown.

As used herein, the terms "polymer composition" or "homopolymer composition" or "copolymer composition" are used herein interchangeably and are meant to include at least one synthesized polymer or copolymer, as well as residues from initiators, catalysts and other elements attendant to the synthesis of such polymer, where such residues are understood as not being covalently incorporated thereto. Such residues and other elements considered as part of the polymer composition are typically mixed or co-mingled with the polymer such that they tend to remain with the polymer when it is transferred between vessels or between solvent or dispersion media. A polymer composition can also include materials added after synthesis of the polymer to provide or modify specific properties to such composition.

It should further be noted that the terms "polymer composition" and polymer formulation" are used herein interchangeably and shall be construed as being the same.

The term "photodefinable" refers to the characteristic of a material or composition of materials, such as a polymer composition in accordance with embodiments of the present invention, to be formed into, in and of itself, a patterned layer or a structure. In alternate language, a "photodefinable layer" does not require the use of another material layer formed thereover, for example a photoresist layer, to form the aforementioned patterned layer or structure. It will be further understood that a polymer composition having such a characteristic be employed in a pattern forming scheme to form a patterned film/layer or structure. It will be noted that such a scheme incorporates an "imagewise exposure" of the photodefinable material or layer. Such imagewise exposure being taken to mean an exposure to actinic radiation of selected portions of the layer, where non-selected portions are protected from such exposure to actinic radiation.

The phrase "a material that photonically forms a catalyst" refers to a material that, when exposed to "actinic radiation" will break down, decompose, or in some other way alter its molecular composition to form a compound capable of initiating a crosslinking reaction in the polymer, where the term "actinic radiation" is meant to include any type of radiation capable of causing the aforementioned change in molecular composition. For example, any wavelength of ultraviolet or visible radiation regardless of the source of such radiation or radiation from an appropriate X-ray and electron beam source. Non-limiting examples of suitable materials that "photonically form catalyst" include photoacid generators and photobase generators such as are discussed in detail below. It should also be noted that generally "a material that photonically forms a catalyst" will also form a catalyst if heated to an appropriate temperature.

Some embodiments in accordance with the present invention provide polycarbonate polymers that encompass repeating units derived from at least one polycyclic epoxide monomer represented by and selected from the following Formulae (IA), (IB) or (IC):

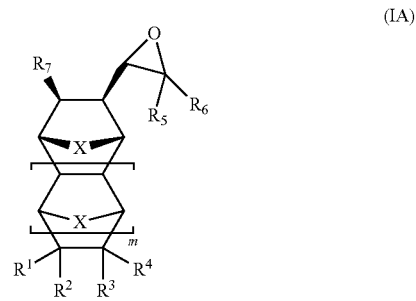

(IA)

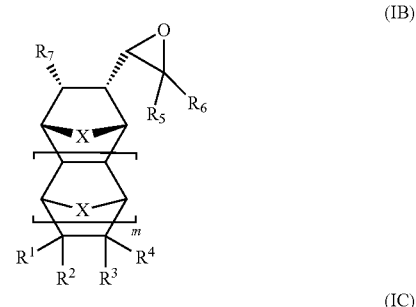

(IB)

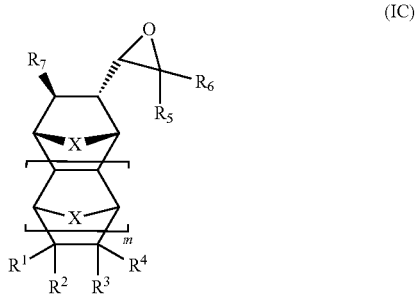

(IC)

For each monomer represented by Formulae (IA), (IB) and (IC), m, X, $R_1$, $R_2$, $R_3$, $R_4$, $R_5$, $R_6$ and $R_7$ are as defined hereinbelow.

In some other embodiments the polycarbonate polymers of this invention encompass not only the repeat units derived from compounds of Formulae (IA), (IB) or (IC) but also one or more of any other known epoxide monomers, including any of the epoxides represented by the following epoxide Formula (ID):

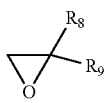
(ID)

Where each occurrence of $R_8$ and $R_9$ independently represents hydrogen, methyl, ethyl, linear or branched $C_3$-$C_{12}$-alkyl, $C_3$-$C_{12}$-cycloalkyl or $R_8$ and $R_9$ taken together with the carbon atom to which they are attached form a $C_3$-$C_{12}$-cycloalkyl ring optionally containing one or more heteroatoms selected from nitrogen, oxygen, sulfur and the like.

Monomers

Embodiments in accordance with the present invention are suitable for the preparation of polymers encompassing a wide range of "polycyclic" repeating units. As a representative example of such a compound or a monomer is "norbornane-oxirane-type" monomer that encompass at least one norbornane moiety such as shown below:

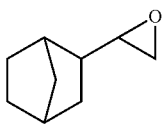

The simplest norbornane-type or polycyclic monomer encompassed by embodiments in accordance with the present invention is the bicyclic monomer, bicyclo[2.2.1]hept-2-ane, commonly referred to as norbornane. However, the term norbornane-type monomer or repeating unit is used herein to mean norbornane itself as well as any substituted norbornane(s), or substituted and unsubstituted higher cyclic derivatives thereof. Representative examples of such monomers include but not limited to bicyclo[2.2.2]oct-2-ane, 7-oxabicyclo[2.2.1]hept-2-ane, 7-thiabicyclo[2.2.1]hept-2-ane, 7-azabicyclo[2.2.1]hept-2-ane, 1,2,3,4,4a,5,8,8a-octahydro-1,4:5,8-dimethanonaphthalene, 1,4,4a,5,6,7,8,8a-octahydro-1,4-epoxy-5,8-methanonaphthalene, and the like.

Thus in accordance with embodiments of this invention there is provided a compound of formula (I):

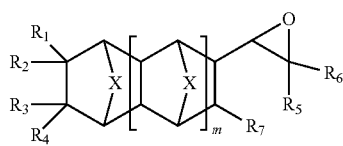
(I)

wherein:
m is an integer from 0 to 2, inclusive;
X is —CH$_2$— or —CH$_2$—CH$_2$;
each occurrence of $R_1$, $R_2$, $R_3$ and $R_4$ independently represents hydrogen, methyl, ethyl, linear or branched $C_3$-$C_{12}$-alkyl, $C_3$-$C_{12}$-cycloalkyl, $C_6$-$C_{12}$-bicycloalkyl, $C_7$-$C_{14}$-tricycloalkyl, $C_{10}$-$C_{14}$-tetracycloalkyl, $C_6$-$C_{10}$-aryl, $C_6$-$C_{10}$-aryl-$C_1$-$C_3$-alkyl, $C_5$-$C_{10}$-heteroaryl, $C_5$-$C_{10}$-heteroaryl-$C_1$-$C_3$-alkyl, $C_1$-$C_{12}$-alkoxy, $C_3$-$C_{12}$-cycloalkoxy, $C_6$-$C_{12}$-bicycloalkoxy, $C_7$-$C_{14}$-tricycloalkoxy, $C_{10}$-$C_{14}$-tetracycloalkoxy, $C_6$-$C_{10}$-aryloxy-$C_1$-$C_3$-alkyl, $C_5$-$C_{10}$-heteroaryloxy-$C_1$-$C_3$-alkyl, $C_6$-$C_{10}$-aryloxy, $C_5$-$C_{10}$-heteroaryloxy, $C_1$-$C_6$-acyloxy and halogen; or $R_1$ and $R_2$ or $R_2$ and $R_3$ or $R_3$ and $R_4$ taken together with the carbon atom to which they are attached form a $C_3$-$C_{12}$-cycloalkyl ring optionally containing one or more hetero atoms selected from nitrogen, oxygen and sulfur;

each occurrence of $R_5$ and $R_6$ independently represents hydrogen, methyl, ethyl, linear or branched $C_3$-$C_{12}$-alkyl; or $R_5$ and $R_6$ taken together with the carbon atom to which they are attached form a $C_3$-$C_{12}$-cycloalkyl ring optionally containing one or more heteroatoms selected from nitrogen, oxygen and sulfur; and $R_7$ represents hydrogen, methyl, ethyl, linear or branched $C_3$-$C_{12}$-alkyl and phenyl.

As noted above, several of the compounds of formula (I) can exist in more than one stereoisomeric form. Accordingly, all forms of stereoisomers of compound of formula (I), including enantiomers, diastereomers or racemic mixtures of compound of formula (I) are part of this invention.

As further noted above certain compounds of formula (I) are already known in the literature, such compounds are specifically excluded from the embodiments of compounds of formula (I). In particular the following compounds are disclosed in JP 60079038 (published May 4, 1985):

2-(bicyclo[2.2.1]heptan-2-yl)oxirane;
2-(6-phenylbicyclo[2.2.1]heptan-2-yl)oxirane; and
2-(5-phenylbicyclo[2.2.1]heptan-2-yl)oxirane.

In some embodiments in accordance with the present invention, the compound represented by formula (I) is defined by the following substituents: m is 0 or 1; X is CH$_2$; each occurrence of $R_1$, $R_2$, $R_3$ and $R_4$ independently represents hydrogen, cyclohexyl, bicyclo[2.2.1]heptanyl and decahydro-1,4:5,8-dimethanonaphthalenyl; and each occurrence of $R_5$ and $R_6$ independently represents hydrogen, methyl and ethyl and $R_7$ is hydrogen.

A few of the representative compounds encompassed by compound of formula (I) of this invention without any limitation are listed below:

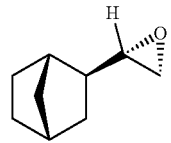

(S)-2-((1S,2S,4R)-bicyclo[2.2.1]heptan-2-yl)oxirane (exo-NBaneOx);

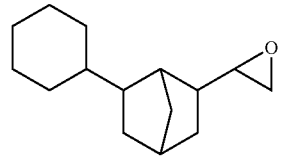

2-(6-cyclohexylbicyclo[2.2.1]heptan-2-yl)oxirane;

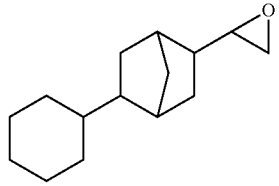

2-(5-cyclohexylbicyclo[2.2.1]heptan-2-yl)oxirane;

-continued

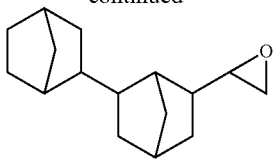

2-([2,2'-bi(bicyclo[2.2.1]heptan)]-6-yl)oxirane;

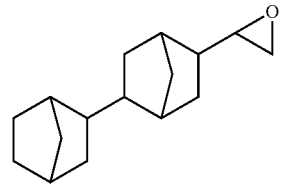

2-([2,2'-bi(bicyclo[2.2.1]heptan)]-5-yl)oxirane;

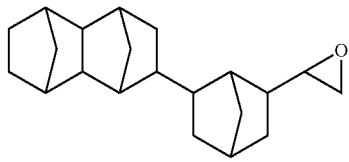

2-(6-(decahydro-1,4:5,8-dimethanonaphthalen-2-yl)bicyclo[2.2.1]heptan-2-yl)oxirane;

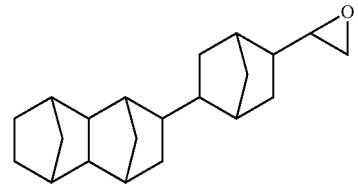

2-(5-(decahydro-1,4:5,8-dimethanonaphthalen-2-yl)bicyclo[2.2.1]heptan-2-yl)oxirane; and

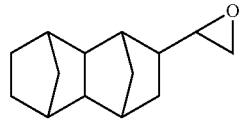

2-(decahydro-1,4:5,8-dimethanonaphthalen-2-yl)oxirane; and

2-(tricyclo[2.2.1.0$^{2,6}$]heptan-3-yl)oxirane.

As noted above, several of the compounds of formula (I) exists in various stereoisomeric forms and all such forms are part of the embodiment of this invention. More specifically, 2-(bicyclo[2.2.1]heptan-2-yl)oxirane can exist in various stereoisomeric forms and some of which, without any limitation are listed below:

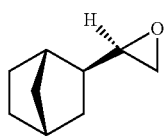

(R)-2-((1S,2S,4R)-bicyclo[2.2.1]heptan-2-yl)oxirane;

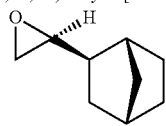

(S)-2-((1R,2R,4S)-bicyclo[2.2.1]heptan-2-yl)oxirane;

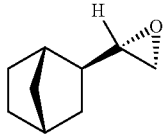

(S)-2-((1S,2S,4R)-bicyclo[2.2.1]heptan-2-yl)oxirane; and

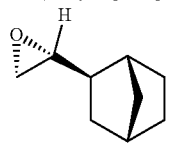

(R)-2-((1R,2R,4S)-bicyclo[2.2.1]heptan-2-yl)oxirane.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein.

Typically, the compounds of formula (I) can be prepared by subjecting a precursor vinylic compound of formula (II) to suitable epoxidation conditions as summarized in Scheme I. For example, such epoxidation reactions can be carried out by reacting compound of formula (II) with any of the known peroxides or peracids, such as for example, m-chloroperbenzoic acid at suitable reaction temperature in an organic solvent.

Scheme I

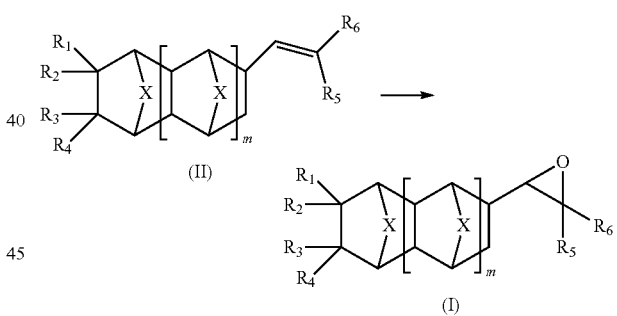

Polymers

Embodiments in accordance with the present invention also provide a polymer comprising the repeat units of formula (III), said repeat unit is derived from a compound of formula (I):

(III)

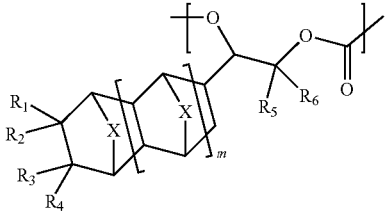

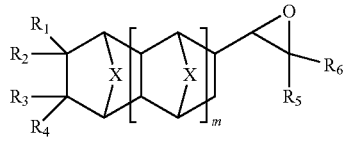

(I)

wherein:

m is an integer from 0 to 2, inclusive;

X is —CH$_2$— or —CH$_2$—CH$_2$;

each occurrence of R$_1$, R$_2$, R$_3$ and R$_4$ independently represents hydrogen, methyl, ethyl, linear or branched C$_3$-C$_{12}$-alkyl, C$_3$-C$_{12}$-cycloalkyl, C$_6$-C$_{12}$-bicycloalkyl, C$_7$-C$_{14}$-tricycloalkyl, C$_{10}$-C$_{14}$-tetracycloalkyl, C$_6$-C$_{10}$-aryl, C$_6$-C$_{10}$-aryl-C$_1$-C$_3$-alkyl, C$_5$-C$_{10}$-heteroaryl, C$_5$-C$_{10}$-heteroaryl-C$_1$-C$_3$-alkyl, C$_1$-C$_{12}$-alkoxy, C$_3$-C$_{12}$-cycloalkoxy, C$_6$-C$_{12}$-bicycloalkoxy, C$_7$-C$_{14}$-tricycloalkoxy, C$_{10}$-C$_{14}$-tetracycloalkoxy, C$_6$-C$_{10}$-aryloxy-C$_1$-C$_3$-alkyl, C$_5$-C$_{10}$-heteroaryloxy-C$_1$-C$_3$-alkyl, C$_6$-C$_{10}$-aryloxy, C$_5$-C$_{10}$-heteroaryloxy, C$_1$-C$_6$-acyloxy and halogen; or R$_1$ and R$_2$ or R$_2$ and R$_3$ or R$_3$ and R$_4$ taken together with the carbon atom to which they are attached form a C$_3$-C$_{12}$-cycloalkyl ring optionally containing one or more hetero atoms selected from nitrogen, oxygen and sulfur;

each occurrence of R$_5$ and R$_6$ independently represents hydrogen, methyl, ethyl, linear or branched C$_3$-C$_{12}$-alkyl; or R$_5$ and R$_6$ taken together with the carbon atom to which they are attached form a C$_3$-C$_{12}$-cycloalkyl ring optionally containing one or more hetero atoms selected from nitrogen, oxygen and sulfur.

In some of the embodiments the polymer of formula (III) can be defined by the following substituents: m is 0 or 1; X is CH$_2$; each occurrence of R$_1$, R$_2$, R$_3$ and R$_4$ independently represents hydrogen, phenyl, cyclohexyl, bicyclo[2.2.1]heptanyl and decahydro-1,4:5,8-dimethanonaphthalenyl (also referred to as tetracyclododecyl (TD) group); and each occurrence of R$_5$ and R$_6$ independently represents hydrogen, methyl and ethyl.

In yet another embodiment, the polymer of formula (III) can contain a repeat unit which is derived from a compound or monomer selected from one or more of the following:

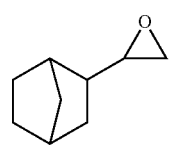

2(bicyclo[2.2.1]heptan-2-yl)oxirane;

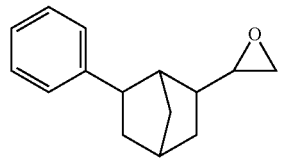

2-(6-phenylbicyclo[2.2.1]heptan-2-yl)oxirane; and

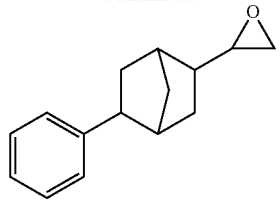

2-(5-phenylbicyclo[2.2.1]heptan-2-yl)oxirane.

In yet another embodiment any of the compounds of formula (I) described above can also be used as monomers to make the polymers of formula (III) of this invention. Specifically, without any limitation such compounds of formula (I) may be enumerated as follows:

(S)-2-((1S,2S,4R)-bicyclo[2.2.1]heptan-2-yl)oxirane;
(R)-2-((1S,2S,4R)-bicyclo[2.2.1]heptan-2-yl)oxirane;
(S)-2-((1R,2R,4S)-bicyclo[2.2.1]heptan-2-yl)oxirane;
(R)-2-((1R,2R,4S)-bicyclo[2.2.1]heptan-2-yl)oxirane;
2-(6-cyclohexylbicyclo[2.2.1]heptan-2-yl)oxirane;
2-(5-cyclohexylbicyclo[2.2.1]heptan-2-yl)oxirane;
2-([2,2'-bi(bicyclo[2.2.1]heptan)]-6-yl)oxirane;
2-([2,2'-bi(bicyclo[2.2.1]heptan)]-5-yl)oxirane;
2-(6-(decahydro-1,4:5,8-dimethanonaphthalen-2-yl)bicyclo[2.2.1]heptan-2-yl)oxirane;
2-(5-(decahydro-1,4:5,8-dimethanonaphthalen-2-yl)bicyclo[2.2.1]heptan-2-yl)oxirane; and
2-(decahydro-1,4:5,8-dimethanonaphthalen-2-yl)oxirane.

In another embodiment of this invention the polycarbonate of this invention includes repeat units of formula (IV) formed from the reaction of carbon dioxide with one or more epoxide monomer of formula (ID) in addition to the repeats of formula (III).

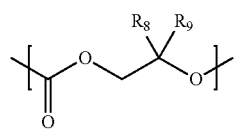

(IV)

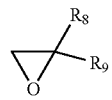

(ID)

Representative examples of epoxides of formula (ID), without any limitation, include the following:

2-methyloxirane;
2-ethyloxirane;
2-isopropyloxirane;
2-(tert-butyl)oxirane;
2-(tert-pentyl)oxirane;
2-cyclopentyloxirane;
2-cyclohexyloxirane;
2-cycloheptyloxirane;
2-cyclooctyloxirane;
1-oxaspiro[2.5]octane;
1-oxaspiro[2.7]decane; and
2-(1-admantyl)oxirane.

The polycarbonate polymers of formula (III) feature alternating repeat units derived from each unit of the compound of formula (I) reacted with a molecule of carbon dioxide. The polymers of formula (III) formed according to this invention generally exhibit a weight average molecular weight ($M_w$) of at least about 1,000. In another embodiment, the polymer of formula (III) of this invention has a $M_w$ of at least about 50,000. In yet another embodiment, the polymer of formula (III) has a $M_w$ of at least about 500,000. Generally, the larger the $M_w$, the better the mechanical properties and thus feature not only better film forming properties but also feature good mechanical properties. Thus in an embodiment of this invention the polymer of formula (III) exhibits a weight average molecular weight of from about 1,000 to about 300,000. The weight average molecular weight ($M_w$) and the number average molecular weight ($M_n$) are generally determined by gel permeation chromatography (GPC) using polystyrene calibration standards. However, any of the other known methods can also be used to determine $M_w$ and $M_n$. From this the polydispersity index (PDI) of the polymer can also be determined ($M_w/M_n$). In some embodiments of this invention the polydispersity index of the polymers of formula (III) of this invention generally is from about 1 to 5, in some other embodiments of this invention the polydispersity index of the polymers of formula (III) of this invention generally is from about 1 to 3, and yet in some other embodiments of this invention the polydispersity index of the polymers of formula (III) of this invention generally is from about 1 to 2.

As noted above, the polymer of formula (III) exhibit better thermal properties than those of conventional polycarbonates, such as PPC. In some embodiments of this invention, the polymer of formula (III) exhibits a glass transition temperature ($T_g$) of at least about 60° C. In another embodiment of this invention, the polymer of formula (III) exhibits a $T_g$ of at least about 80° C. In yet another embodiment of this invention, the polymer of formula (III) exhibits a $T_g$ of at least about 100° C.

In another embodiment the polycarbonate of this invention containing both the repeat units of formula (III) and (IV) exhibit tailored thermal properties. That is, any desirable thermal properties can be achieved by suitable incorporation of repeat units of formula (III) and (IV). Thus in one of the embodiments of this invention the polycarbonate of this invention is comprised of 1:99 to 99:1 molar ratio of the repeat units of formula (III) and (IV) respectively. In another embodiment of this invention, the molar ratios of repeat units (III) and (IV) are respectively from 20:80 to 80:20. In yet another embodiment of this invention, the molar ratios of repeat units (III) and (IV) are respectively from 40:60 to 60:40.

In another embodiment of this invention there is also provided a process for making a polymer of formula (III). The process involves reacting a compound of formula (I) with carbon dioxide in the presence of a ligand-supported metal catalyst optionally in the presence of a suitable solvent. Any one of the compounds of formula (I) including the compounds which are known in the literature as described above can be used to prepare the polymers of formula (III). A similar process can be employed to make the co-polycarbonates containing both repeat units of formula (III) and (IV) by employing the desirable amounts of monomers of formula (I) and (II).

As noted, any of the suitable solvents that would not only dissolve the ligand-supported metal catalyst but also would bring about the reaction of compound of formula (I) with carbon dioxide can be employed. Suitable solvents generally include non-oxophilic solvents such as halogenated solvents or hydrocarbon solvents and mixtures thereof. Representative examples of solvents include, without any limitation, dichloromethane, 1,2-dichloroethane, chloroform, carbon tetrachloride, and the like.

Any of the ligand-supported metal catalyst that can bring about the reaction of compound of formula (I) with carbon dioxide can be used to form the polymer of formula (III). Typically, such ligand-supported metal catalyst can be made from any of the metals selected from the group consisting of chromium, manganese, iron, cobalt, nickel, ruthenium, rhodium, palladium, iridium, platinum and zinc.

It has now been found that ligand-supported metal catalysts derived from cobalt are advantageously useful in the process of this invention. Such cobalt metal complex catalysts may be represented by formulae (V) or (VI):

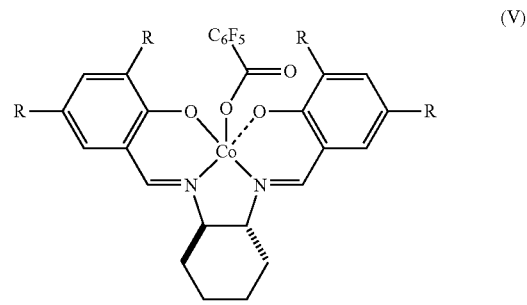

(V)

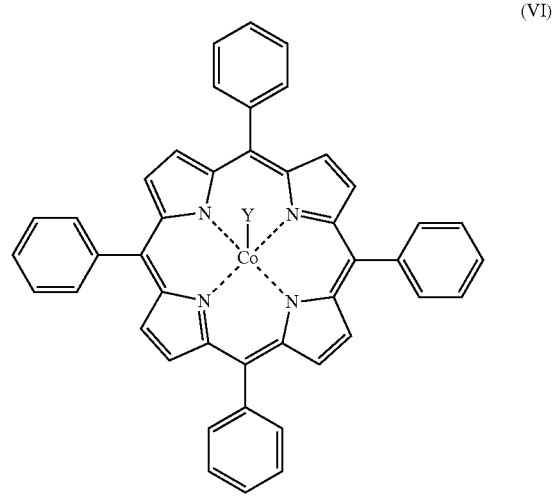

(VI)

Wherein R is methyl, ethyl, linear or branched $C_3$-$C_{12}$-alkyl, $C_3$-$C_{12}$-cycloalkyl and $C_6$-$C_{10}$-aryl; and wherein V is halogen, acetate, trifluoroacetate, benzoate, tosylate, triflate, mesylate, nitrate, $C_6F_5CO_2$ and azide. In one embodiment of the process of this invention, such catalyst employed is a cobalt complex of formula (V) wherein R is tert-butyl. In another embodiment of the process of this invention, such catalyst employed is a cobalt complex of formula (VI) wherein Y is chlorine.

Advantageously, it has further been found that various co-catalysts can also be employed in the process of this invention. Suitable examples of such co-catalysts include without any limitation pyridine, N,N-dimethylpyridin-4-amine (DMAP), 4-(pyrrolidin-1-yl)pyridine (4-PYP), 2,3,4,6,7,8-hexahydropyrrolo[1,2-a]pyrimidine (DBN), 2,3,4,6,7,8,9,10-octahydropyrimido[1,2-a]azepine (DBU), 2,3,4,6,7,8-hexahydro-1H-pyrimido[1,2-a]pyrimidine (TBD), 1,1,1-triphenyl-N-(triphenylphosphoranylidene)-phosphoraniminium halide (PPNX), 1,1,1-triphenyl-N-(triphenylphosphoranylidene)-phosphoraniminium azide (PPNN$_3$), tetraethylammonium acetate and tricyclohexylphosphine. The structures of some of these co-catalysts are provided below.

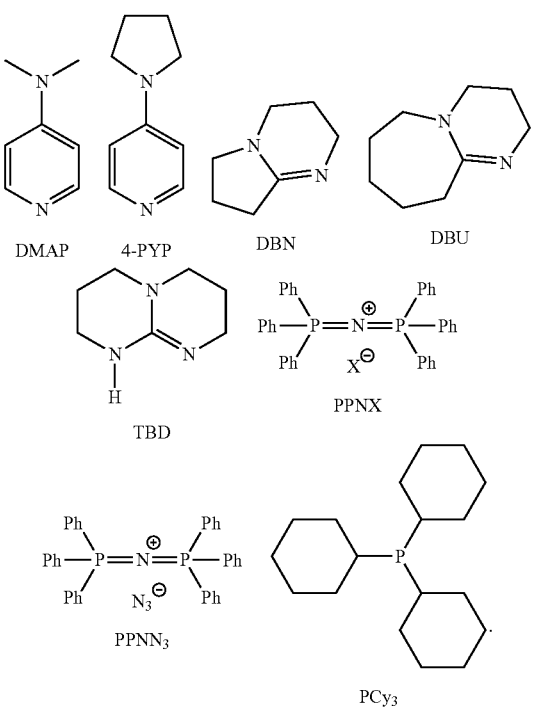

DMAP  4-PYP  DBN  DBU

TBD  PPNX

PPNN₃  PCy₃

In one of the embodiments the co-catalyst employed is of the formula (VII):

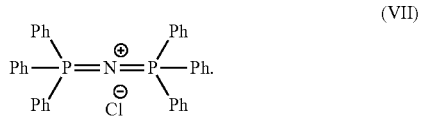

(VII)

In another embodiment of this invention there is further provided a sacrificial polymer composition comprising: one or more polymer of formula (III) (or a copolymer containing repeat units of formula (III) and (IV)) as described herein; one or more of a photoacid generator (PAG) or photobase generator (PBG) or mixtures thereof; and a solvent. In one of the embodiment the sacrificial polymer composition of this invention can further comprise a thermally activated acid generator (TAG). The sacrificial polymer composition embodiments according to the present invention can encompass a single polycarbonate polymer or two or more polycarbonate polymer embodiments according to the present invention.

In another embodiment, the sacrificial polymer composition comprises a polymer of formula (III) as described herein; one or more of a thermally activated acid generator (TAG) or a thermally activated base generator (TBG) and a solvent.

For some embodiments according to the present invention, the sacrificial polymer composition can optionally further include one or more solvents. Solvent can be present in an amount of from, for example, 10 to 99 percent by weight, or 40 to 90 percent by weight, or 50 to 80 percent by weight, based on the total weight of the sacrificial polymer composition. Various solvents can be employed to form the sacrificial polymer compositions of this invention. Representative examples of such solvents without any limitation include the following: anisole, n-butyl acetate (BuOAc), dimethylacetamide (DMAc), cyclopentanone, cyclohexanone, gamma butyrolactone (GBL), propyleneglycol-monomethylether acetate (PGMEA) and mixtures thereof.

Photoacid generators used in the sacrificial composition embodiments according to the present invention, generate an acid, such as but not limited to a protonic acid, after exposure to actinic light, such as but not limited to ultraviolet light, and/or elevated temperature, such as but not limited to temperatures of at least 100° C. Thermal acid generators used in sacrificial composition embodiments according to the present invention, generate an acid, such as but not limited to a protonic acid, after exposure to elevated temperature, such as but not limited to, temperatures of at least 100° C. With some embodiments, the thermal acid generator is selected from thermal acid generators that are also photoactive, such as but not limited to photoacid generators. With some embodiments, the thermal acid generator is selected from thermal acid generators that are not photoactive, such as but not limited to thermal acid generators that are not photoacid generators.

Photoacid generators and thermal acid generators, that can be included in sacrificial polymer composition embodiments according to the present invention, generate one or more acids that result in depolymerization, such as but not limited to catalytic depolymerization, of the polycarbonate polymer embodiments according to the present invention. As used herein, the term "depolymerization" means the polycarbonate polymer is at least partially broken down into smaller units each having a molecular weight less than the molecular weight of the polycarbonate polymer prior to depolymerization. Such depolymerized units, generally having properties distinct from those of the polymers before depolymerization, include but are not limited to: the monomers from which the polymer was derived; polycarbonate oligomers; hydroxyl-terminated polycyclic carbonate oligomers; polycyclic carbonates; polycyclic ethers; cyclic carbonates; cyclic ethers; and/or gasses, such as but not limited to CO and/or $CO_2$.

Photoacid generators that can be included in the sacrificial composition can be selected from, for example, halonium salts and/or sulfonium salts. Examples of photoacid generators that can be included in sacrificial composition embodiments according to the present invention include, but are not limited to: 4-methylphenyl[4-(1-methylethyl)phenyl]iodonium tetrakis(pentafluorophenyl)borate; bis(4-tert-butylphenyl)iodonium triflate; di(4-tert-butyl)phenyliodonium bis(perfluoromethane-sulfonyl)imide; di(4-tert-butylphenyl) iodonium tris(perfluoromethanesulfonyl)methide; tris(4-tert-butylphenyl)sulfonium tetrakis(pentafluorophenyl) borate; tris(4-tert-butylphenyl)sulfonium hexafluorophosphate; triphenylsulfonium hexafluoroantimonate; triphenylsulfonium bis(perfluoromethanesulfonyl) imide; triphenylsulfonium tris(perfluoromethanesulfonyl) methide; tris[4-[(4-acetylphenyl)thio]phenyl]sulfonium tris ((trifluoromethyl)sulfonyl)methanide (trade designation, GSID-26-1); tris[4-[(4-acetylphenyl)thio]phenyl]sulfonium tetrakis(pentafluorophenyl)borate (trade designation, IRGACURE® PAG 290); triphenylsulfonium tris[(trifluoromethyl)sulfonyl]methanide (trade designation, TPS-C1); triphenylsulfonium 4,4,5,5,6,6-hexafluorodihydro-4H-1,3,2-dithiazine-1,1,3,3-tetraoxide (trade designation, TPS-N3); and combinations of two or more thereof. GSID-26-1 and IRGACURE® PAG 290 are commercially available from BASF Corporation. TPS-C1 and TPS-N3 are commercially available from DayChem Laboratories, Inc.

Thermal acid generators that can be included in sacrificial polymer composition embodiments according to the present invention include, but are not limited to: thermal acid generators that include a cation selected from ammonium, pyridinium, halonium, such as but not limited to iodonium, and sulfonium, and a weakly coordinating anion; N-sulfoximides; and combinations of two or more thereof. Generally the acids from which the weakly coordinating anions are formed have a pKa of less than 2.0 while in some other embodiments the acid having a pKa of 0.75 or less and for still other embodiments the acid having a pKa of −0.5 or less are employed. Examples of weakly coordinating anions include anions of strong acids, which can have pKa values of less than or equal to −2, and which can include, but are not limited to: hexafluoroarsenate ($AsF_6^-$); hexafluoroantimonate ($SbF_6^-$); hexafluorophosphate ($PF_6^-$); perfluoroalkyl sulfonates, such as, trifluoromethane sulfonate ($CF_3SO_3^-$), perfluorobutyl sulfonate ($C_4F_9SO_3^-$), and perfluorooctylsulfonate ($C_8F_{17}SO_3^-$); bis(perfluoroalkylsulfonyl)imide anions, such as, bis(trifluormethylsulfonyl)imide anion, $(CF_3SO_2)_2N^-$; tris(perfluoroalkylsulfonyl)-methides, such as, tris(trifluoromethylsulfonyl)methide, $(CF_3-SO_2)_3C^-$; tetrakis-(pentafluorophenyl)borate, $(C_6F_5)_4B^-$; tetrakis(3,5-perfluoroalkyl-phenyl)borates, such as, tetrakis(3,5-trifluoromethylphenyl)borate, $(3,5-(CF_3)_2C_6H_3)_4B^-$; and combinations of two or more thereof.

Various aforementioned examples of PAGs, PBGs and TAGs are enumerated structurally below without any limitation or preferences:

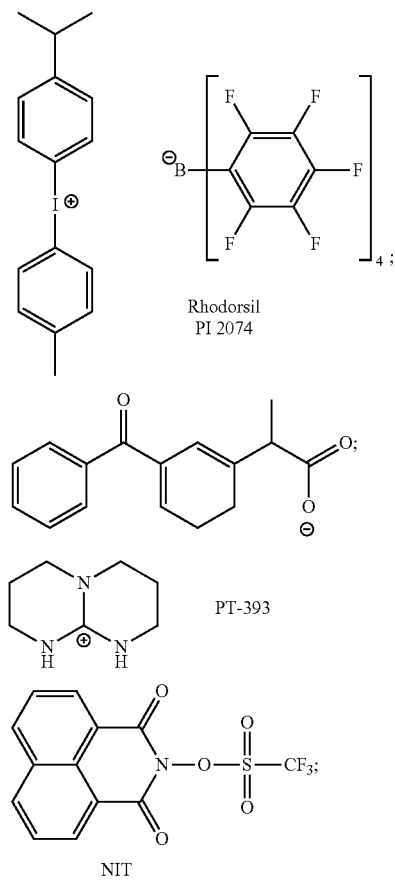

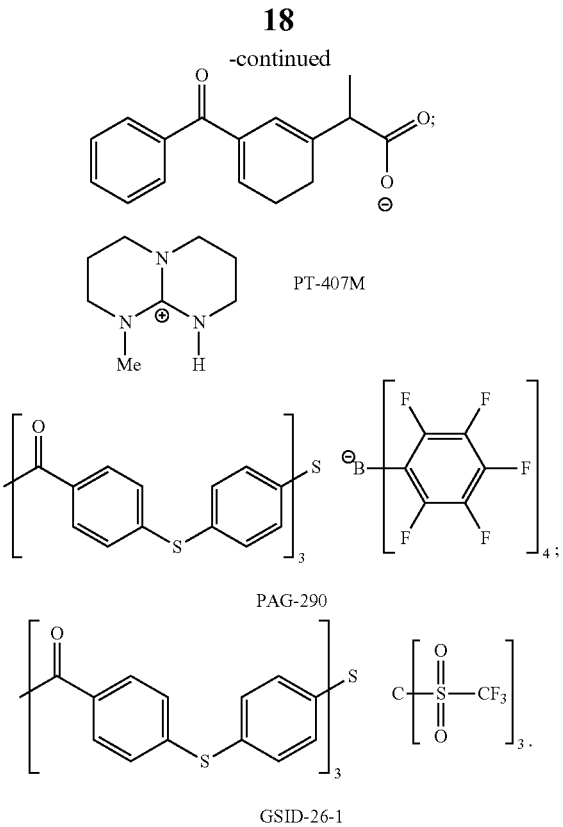

Ammonium salts from which the thermal acid generator can be selected, can be represented by the following general formula TAG-1, $$R^{10}R^{11}R^{12}R^{13}N^+ \quad (A^-)$$ TAG-1

With reference to formula TAG-1, $R^{10}R^{11}R^{12}R^{13}N^+$ represents an ammonium cation in which $R^{10}$, $R^{11}$, $R^{12}$ and $R^{13}$ are each independently selected from hydrogen and hydrocarbyl. In some embodiments no more than one of $R^{10}$, $R^{11}$, $R^{12}$ and $R^{13}$ is selected from hydrogen. In some embodiments, each of $R^{10}$, $R^{11}$, $R^{12}$ and $R^{13}$ are independently selected from hydrocarbyl, and none of $R^{10}$, $R^{11}$, $R^{12}$ and $R^{13}$ are hydrogen. The hydrocarbyls from which each $R^{10}$, $R^{11}$, $R^{12}$ and $R^{13}$ can be independently selected include those classes and examples as described above. The symbol $A^-$ of formula TAG-1 represents a weakly coordinating anion, which can be selected from those classes and examples as described previously herein.

With further reference to formula TAG-1, at least one of $R^{10}$, $R^{11}$, $R^{12}$ and $R^{13}$ includes an ether group represented by $-O-R^{14}$, where $R^{14}$ is a hydrocarbyl group. For some embodiments, $R^{10}$ and $R^{11}$ are each methyl ($-CH_3$), $R^{12}$ is phenyl ($-C_6H_5$) and $R^{13}$ is 4-methoxybenzyl

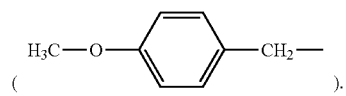

Pyridinium salts from which the thermal acid generator can be selected, can be represented by the following general formula TAG-2,

TAG-2

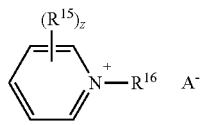

With reference to formula TAG-2, $(R^{15})_z C_5 H_{(5-z)} N^{+} - R^{16}$ represents a pyridinium cation, in which $R^{15}$, if present, is independently selected for each z from hydrocarbyl, $R^{16}$ is independently selected from hydrocarbyl or hydrogen, and z is from 0 to 5, such as 0, 1, 2, 3, 4 or 5. The hydrocarbyls from which each of $R^{15}$ and $R^{16}$ can be independently selected include those classes and examples as described previously herein. The symbol $A^-$ of formula TAG-2 represents a weakly coordinating anion, which can be selected from those classes and examples as described previously herein.

N-sulfoximides from which the thermal acid generator can be selected include, but are not limited to, those represented by the following general formula TAG-3,

TAG-3

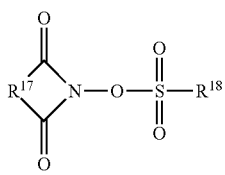

With formula TAG-3 $R^{17}$ is a hydrocarbyl linking group having at least two adjacent carbons, at least two adjacent carbons of $R^{18}$ optionally having bonded thereto a fused ring selected from non-aromatic rings, polycyclic rings and aromatic rings, and $R^{18}$ is selected from halohydrocarbyl and perhalocarbyl. Examples of N-sulfoximides from which the thermal acid generator can be selected include, but are not limited to, those represented by the following general formulae TAG-4 through TAG-8.

TAG-4

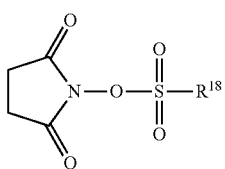

TAG-5

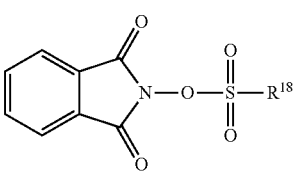

TAG-6

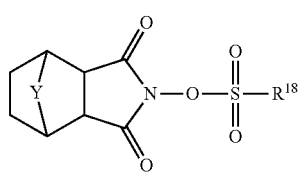

TAG-7

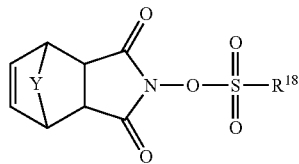

TAG-8

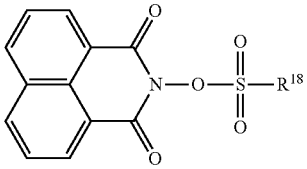

With reference to general formulae TAG-3 through TAG-8, $R^{18}$ in each case independently represents a halohydrocarbyl group. In an embodiment, $R^{18}$ of general formulae TAG-3 through TAG-8 independently represents a perhalocarbyl group, such as but not limited to perfluoromethyl, perfluoroethyl, perfluoropropyl, perfluorobutyl, perfluoropentyl, perfluorohexyl, perfluoroheptyl and perfluorooctyl. In an embodiment, $R^{18}$ of general formulae TAG-3 through TAG-8 is trifluoromethyl.

With reference to general formulae TAG-6 and TAG-7, Y in each case is independently selected from —$CH_2$—, —$CH_2$—$CH_2$— and —O—. For some embodiments, Y of general formulae TAG-6 and TAG-7 is in each case independently selected from —$CH_2$— and —O—.

Halonium and sulfonium cations from which the cations of the thermal acid generator can be selected include those known to one skilled in the art. Typically, halonium cations, such as but not limited to iodonium, are substituted with two aryl groups, such as but not limited to phenyl or substituted phenyl groups, such as but not limited to 4-tert-butylphenyl. Sulfonium cations are typically substituted with three aryl groups, such as but not limited to phenyl or substituted phenyl groups, such as but not limited to 4-tert-butylphenyl. Examples of halonium and sulfonium cations include, but are not limited to, those recited previously herein with regard to the photoacid generator, such as but not limited to bis(4-tert-butylphenyl)iodonium and triphenylsulfonium.

Sulfonium salts from which the thermal acid generator can be selected include, but are not limited to, those represented by the following general formula TAG-9.

TAG-9

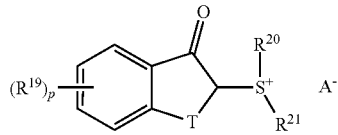

With reference to general formula TAG-9, $R^{19}$ can independently for each p be selected from a halo group, a hydrocarbyl group, or $R^{22}$—O—, where $R^{22}$ is a hydrocarbyl group, and p is from 0 to 4, such as 0, 1, 2, 3 or 4. The groups $R^{20}$ and $R^{21}$ of general formula TAG-9 can each be independently selected from hydrocarbyl, or can together form a ring, such as but not limited to a 5 or 6 membered ring. For example, $R^{20}$ and $R^{21}$ can each be independently selected from methyl, ethyl, cyclopentyl, cyclohexyl and 2-norbornyl. The T group of general formula TAG-9 can be selected from —$CH_2$—, —$C_2H_4$— or —$CH_2$—O—. The symbol A⁻ of formula TAG-9 represents a weakly coordinating anion, which can be selected from those classes and examples as described previously herein.

The sacrificial polymer composition of this invention further comprises optional additives selected from the group consisting of sensitizer, adhesion promoters, antioxidants, antioxidant synergists and fillers.

A representative examples of such optional additives are selected from 1-chloro-4-propylthioxanthane (CPTX), isopropyl thioxanthone (ITX), phenothiazine, benzoquinone and 1,1,1-tris(hydroxymethyl)propane (THMP).

For some embodiments according to the present invention, the polycarbonate polymer can be present in the sacrificial polymer composition in an amount of from 1 to 99.5 percent by weight, or 1 to 75 percent by weight, or 1 to 60 percent by weight, based on the total weight of the sacrificial polymer composition. The balance of percent weights is made up by the carrier solvent, photoacid generator and/or thermal acid generator, and optional components including, but not limited to, optional antioxidant, optional antioxidant synergist, optional co-solvent, and/or optional fluxing agent, such as formic acid.

Generally, any desirable amounts of PAGs, PBGs or TAGs, as described herein can be employed with the sacrificial polymer composition of this invention. In one embodiment, the PAG or PBG loading is from about 0.15 parts per hundred polymer to 10 parts per hundred polymer, or from 0.75 parts per hundred polymer to 6 parts per hundred polymer, or from 1 parts per hundred polymer to 3 parts per hundred polymer.

For some embodiments according to the present invention, the sacrificial polymer composition can be a photodefinable sacrificial polymer composition which is generally a positive-tone material. The photodefinable sacrificial polymer composition is typically applied in the form of a coating over a substrate, such as, a silicon chip or wafer to form a layer or film thereon. Typically, after forming such layer, the composition is image-wise exposed to actinic radiation of an appropriate wavelength and energy. In the case of a positive tone photodefinable sacrificial polymer composition, those portions exposed to actinic light passing through the photomask are removed during a development step, including but not limited to solvent washing or thermal decomposition, and the unexposed portions are retained on the substrate.

The photomask can be a gray scale photomask. The gray scale photomask encodes an optical density profile into the underlying photodefinable sacrificial polymer composition, and thereby defines a three-dimensional photodefined structure therein. Actinic light passing through the gray scale photomask typically penetrates at variable depths into the underlying photodefinable sacrificial polymer composition, thereby resulting in the formation of three-dimensional structures in the subsequently developed coating.

The photosensitive composition embodiments of the present invention generally encompass a photoacid generator, as has been described previously herein. As discussed previously herein, upon exposure to actinic radiation of an appropriate wavelength and energy, the photoacid generator generates an acid that causes at least partial depolymerization of the sacrificial polycarbonate polymer. The result of such depolymerization being a lowering of the decomposition temperature of such exposed regions, while those portions that are not exposed are not depolymerized and retain the polymer's original decomposition temperature. Generally such depolymerization also increases the solubility of exposed regions, as compared to unexposed regions, thus allowing for a dissolution-based pattern development process to be employed.

As discussed previously herein with regard to polycarbonate polymer embodiments in accordance with the present invention, sacrificial polymer composition embodiments according to the present invention can be characterized with regard to the temperature at which the polymer depolymerizes or decomposes. This temperature can be referred to as a depolymerization temperature or a decomposition temperature of the sacrificial polymer. Such temperature can be quantified with regard to the $T_{d50}$ decomposition temperatures as further described hereinbelow in the Examples.

In another embodiment, the sacrificial polymer composition of this invention features surprisingly unique thermal properties. In some embodiments of the polymer composition of this invention, it has now been observed that the difference between the thermal decomposition temperature $(T_d)$ of the polymer in the composition after actinic radiation and the glass transition temperature of the polymer $(T_g)$ is generally not greater than 30° C.

As previously described herein, polycarbonates, such as PPC will decompose when heated to temperatures above 225° C., with the 50% weight loss temperature $(T_{d50})$ around 250° C. typically observed in dynamic TGA (10° C./min). Not wishing to be bound by any theory, it is believed that such decomposition is initiated by thermal scission of the carbon-oxygen bond, the weakest bond in the polymer chain, followed by subsequent intramolecular ring closing which generates small cyclic molecules that are volatile and will escape from the film as gaseous species. This mode of decomposition in general requires an initiation temperature of at least >200° C., and offers limited opportunity to define a pattern unless the polycarbonate is used to fill the selected area already patterned by an alternative method.

It has been found that a catalytic amount of acid (H⁺) results in more efficient decomposition as described in Journal of Microelectromechanical Systems, 2003, 12(2), 147-159. As described therein a "catalytic" amount of an acid initiates chain scission of PPC followed by intramolecular "back-biting" to yield propylene carbonate, propylene oxide, acetone, and carbon dioxide as decomposition products. Irradiation of a formulation of the polycarbonate with a photoacid generator (PAG) is an efficient means of introducing the acid catalyst only in the exposed areas, thus providing a photodefinable patterning opportunity.

Alternatively, a base (:B in equation below, e.g., OH⁻, OR⁻, R₃N) could be used to initiate polymer chain scission and allow subsequent intramolecular formation of small cyclic molecules as shown in the equation below. Thus it has been our working hypothesis that selected photobase generators (PBG) will be equally effective as light-induced catalyst initiators in photodefinable applications.

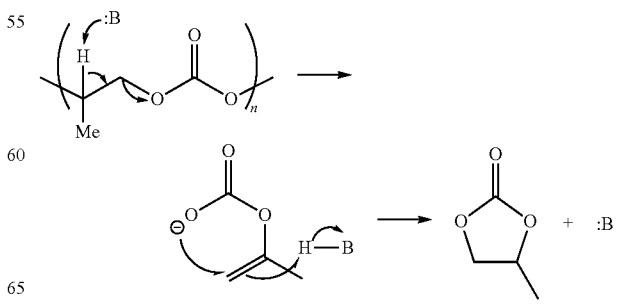

While it has been generally believed that acid generators are photo-responsive, the bases released from base generators were relatively weak and in no way comparable to the superacid typically derived from the acid generators. The photobase generators PT-393 and PT-407M as described herein releases some of the strongest organic bases, e.g., TBD and MTBD, with p$K_a$ of their conjugated acids (as shown below) >20 in acetonitrile (J. Org. Chem. 2005, 70, 1019-1028).

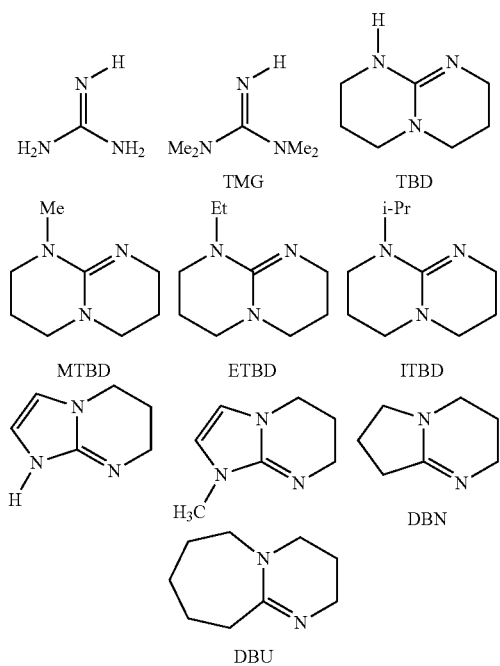

We believe that these bases are strong enough to deliver comparable or even improved polymer decomposition performance as their acid counterparts and leave less residue after development because the catalyst-related species generated upon UV exposure are all considered small organic molecules.

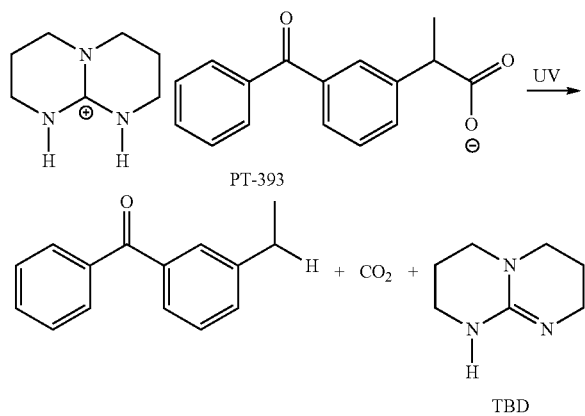

From the examples that follows, it has now been surprisingly found that $T_{d50}$ of polycarbonate derived from (exo-PNBaneEC) with PT-393 was 171° C. This data is comparable to the $T_{d50}$ of 185° C. from PPC with the same loading of PT-393. While no UV exposure is applied in this comparative set of examples, it shows that the thermal decomposition of exo-PNBaneEC is comparable to PPC. With the rigid norbornane side chain installed in exo-PNBaneEC that gives a much higher polymer $T_g$, it can be envisioned that some polycarbonates derived from the epoxide compounds of formula (I) will give a high enough $T_g$ that is comparable to the decomposition temperature ($T_d$) of a UV-exposed PAG or PBG-formulated material. A match of $T_g$ with the $T_d$ of the exposed material reduces issues due to thermal flow, and gives the best retention of pattern fidelity and image resolution possible. Our invention includes polycarbonates with high $T_g$ that is adjustable by changing the rigid side chain derived from the epoxide monomer. As shown from the Examples that follows, stereospecific components can also be introduced to attain specific target properties. Furthermore, the selection and loading of the photoactive additive can be optimized to give the best match of exposed $T_d$ to the $T_g$ of the material, thus delivering a photoimageable system with sufficient patterning resolution.

In further accordance with embodiments of the present invention, there is also provided a method of forming a structure. The structure forming method encompasses forming a three-dimensional structure on a surface of a substrate, where the three-dimensional structure typically includes a sacrificial polymer composition as described above. An overcoat layer is applied over the three-dimensional structure where such overcoat layer is essentially transparent to the appropriate wavelength of radiation that can activate the photoacid generator, the exposure to such light can be used to activate such acid generator. However, as many photoacid generators are also thermally activated, generally the substrate having the aforementioned three-dimensional structures is heated to an elevated temperature sufficient to cause depolymerization of the sacrificial polymer and decomposition and vaporization of the products of such depolymerization. Such a process results in the forming of a three-dimensional space interposed between the overcoat layer and the substrate wherever a three-dimensional structure of such sacrificial polymer had resided. Such space is the result of the conversion of the at least partially depolymerized polymer and its depolymerization products into gaseous components that permeate through the overcoat layer. Where such overcoat layer is essentially opaque, the aforementioned three-dimensional structures are not exposed to a light source and are decomposed directly by heating to an appropriate elevated temperature. The elevated temperature being less than a decomposition temperature of the overcoat layer and substrate.

The three-dimensional structures and the corresponding three-dimensional spaces can each independently have any suitable dimensions, such as heights, lengths and/or widths. The three-dimensional structures and the corresponding three-dimensional spaces can each independently have: a height of from 0.01 to 200 micrometers; a width of from 0.01 to 10,000 micrometers; and a length of from 0.01 micrometers to 100 meters. A plurality of three-dimensional structures/three-dimensional spaces, such as but not limited to a plurality of interconnected three-dimensional structures/three-dimensional spaces, can be formed in methods according to embodiments of the present invention, so as to result in larger and/or more intricate three-dimensional structures/three-dimensional spaces, which can include multiple bends and/or curves in the x-, y-, and/or z-planes.

The overcoat layer can have any suitable thickness, provided it possesses the property of allowing any decomposition products of the sacrificial polymer to permeate therethrough. Typically, the overcoat layer has a thickness of from 1 to 500 micrometers, or from 2 to 300 micrometers, or from 5 to 100 micrometers.

In some sacrificial polymer composition embodiments in accordance with the present invention both a photoacid generator and a thermal acid generator are present. For such embodiments the thermal acid generator is provided to ensure decomposition of three-dimensional structures formed from such sacrificial polymer compositions upon heating to an effective elevated temperature, without the need for an exposure step after such structures are overcoated. Such elevated temperature being from 50° C. to 400° C. for some embodiments, from 80° C. to 250° C. for some other embodiments and from 70° C. to 150° C. for still other embodiments.

In accordance with further embodiments of the present invention, there is provided a method of temporarily bonding a first substrate and a second substrate together. The temporary bonding method encompasses forming a multilayered structure that includes the first substrate, the second substrate, and a temporary bonding layer interposed between the first substrate and the second substrate and applying an effective amount of pressure and/or heat to fixably couple the first substrate to the second substrate. The temporary bonding layer includes a sacrificial polymer composition embodiments of the present invention, as described above. Such temporary bonding layer can alternatively be referred to as a temporary adhesive layer.

To decouple or separate the first and second substrates after fixably coupling such substrates, the acid generator of the sacrificial polymer composition is activated, thereby generating an acid which, at least partially depolymerizes the polycarbonate polymer resulting in the lowering of the polymer's molecular weight, thereby at least partially degrading the temporary bonding layer. As a result of this degrading of the bonding layer, the substrates can be effectively separated from one another via any appropriate and effective process, for example by a slide-off or wedge-off debonding process. While such decoupling generally leaves residue of the bonding layer on one or both substrates, advantageously the depolymerized polymer residues are readily removed by one or both of (1) heating the substrates to an elevated temperature sufficient to forming gaseous products of the decomposition of such depolymerized polymer residue and (2) rinsing such substrates with appropriate aqueous and/or organic solvents. As before, the elevated temperature at which such depolymerization is conducted, is less than a decomposition temperature of the first substrate and less than a decomposition temperature of the second substrate.

The temporary bonding layer can be applied in the form of a coating or film to a surface either one or both substrates prior to bringing the substrates together to sandwich the bonding layer and form the multilayered structure. The temporary bonding layer can be applied to such surface(s) using any appropriate coating method, including, but not limited to those described previously herein. The first and second substrates, with the temporary bonding layer interposed there-between can be subjected to any appropriate process (e.g. wafer thinning or planarization) as a multilayered structure and then subsequently debonded by either the aforementioned wedge-off or slide-off processes.

Sacrificial polymer composition embodiments in accordance with the present invention can optionally include a crosslinking agent that is thermally and/or photonically activated. The crosslinking agent forms a three-dimensional crosslink network within the sacrificial polymer composition that can result in an increased polymer decomposition temperature. Such cross-linked polymers are then useful for the fabrication of various microelectronic devices where such an increased decomposition temperature is advantageous (e.g. MEMS devices).

The first and second substrates can each be independently selected from any suitable materials, such as, but not limited to: metals, such as but not limited to copper, aluminum, steel, and metal alloys; inorganic materials, such as but not limited to silicon dioxide, silicon nitride, and aluminum oxide; organic materials, such as but not limited to organic polymers, such as but not limited to crosslinked organic polymer compositions; and combinations of two or more thereof. While temporarily bonded to each other, the first and/or second substrates are typically modified by methods including, but not limited to, machining, such as but not limited to, chemical mechanical polishing or planarization. In particular, the first surface of the first substrate and/or the second surface of the second substrate are modified. For some embodiments, the second substrate is a die, and the first substrate is a semiconductor wafer. If the semiconductor wafer/first substrate is subjected to a wafer thinning process, the active surface of the semiconductor wafer corresponds to the second surface of the first substrate, and is in facing opposition to the first surface of the second substrate. If the semiconductor wafer/first substrate is subjected to a wafer planarization process, the active surface of the semiconductor wafer corresponds to the first surface of the first substrate, and accordingly faces away from the second substrate.

The sacrificial polymer compositions, polycarbonate polymers and methods in accordance with embodiments of the present invention can be used in or in conjunction with numerous applications including, but not limited to: microelectronics, such as but not limited to microprocessor chips, communication chips, and optoelectronic chips; microfluidics; sensors; and analytical devices, such as but not limited to microchromatographic devices.

It is common practice to use photoacid generators to generate a superacid such as H-FABA because the PAG is regarded as being more efficient in generating an acid and can be activated at 365 nm. The strength of the superacid generated enables the spontaneous decomposition of PPC at moderate to high temperatures. One disadvantage is that these PAG contain halogens and heavy metals.

In contrast it is generally accepted that photobase generators have much lower quantum efficiency and also require shorter wavelength (248 nm) for activation. Our photobase generators, such as PT-393 and PT-407M, generate very strong bases ($pK_a$>20 in acetonitrile) and are capable of decomposing PPC at temperatures lower than those compositions that contain PAGs. Advantageously, the PBG of this invention do not contain heavy atoms or groups (e.g., iodine, antimony, borate) that have been known to leave residues unremovable by heat alone. PBGs are included in some of our compositions with the understanding that base generators give cleaner thermal decomposition than halogen-containing acid generators.

There are several advantages foreseen by the practice of the present invention. As a non-limiting example the polymer compositions/formulations provide potentially better image resolution material with good retention of pattern fidelity by reducing thermal flow issues during thermal development due to low $T_g$ of PPC. The family of higher $T_g$ polycarbonates in this invention is clearly modular, and the rigid structure of the polymer backbone can be changed by adjusting the substituted epoxide monomer. This in turn allows proper tailoring of the polymer to fit formulation and application requirements, e.g., dissolution in a specific process solvent and miscibility with selected photoactive additives. The photoactive component, and its loading, in the compositions can also be adjusted. With a proper selection of the photoactive additive to interact with the specific high $T_g$ polycarbonate, a low-temperature post-exposure development can be achieved to yield high resolution patterns with little to no residue.

Polycarbonates formed from NBaneOx and exo-NBaneOx were expected to have the same $T_g$ (~100° C.), but it was not obvious a priori that it will be higher than PPC (40° C.). This is especially the case considering that polycarbonate with a cyclohexyl side chain from cyclohexyl ethylene epoxide only has a $T_g$ of 45° C. The rigid side chains in epoxides compounds of formula (I) in this invention are designed to deliver polycarbonates with $T_g$ much higher than 40° C.

As will be clear from the examples that follows, it is surprising to expect that polycarbonate from exo-PNBaneEC was found to be significantly more soluble in common process solvents, thereby making it useful in the current applications. The stereospecific rigid side chain, with an exo-norbornane isomer as opposed to a mix of exo and endo from NBaneOx, clearly played a role in the solution properties that are important when miscibility with the photoactive components in film generation by spin-coating or spray-coating are considered. It is not uncommon to obtain non-uniform hazy films that are not optically clear when polymer miscibility in a process solvent is poor. Thus, we believe that we have unexpectedly developed a unique polycarbonate that is of high $T_g$ and also soluble in processing solvents.

When exo-PNBaneEC was formulated with PT-393, as mentioned in the last paragraph of Section 5, it was not expected that the $T_{d50}$ (171° C.) was close to or lower than the $T_{d50}$ from PPC (185° C.) obtained under the same conditions. This is surprising considering that the $T_{d50}$ of unformulated exo-PNBaneEC is 290° C., which is about 40° C. higher than that of PPC (250° C.). It was also unexpected that sharp decomposition was observed with both polymers, with 90% material decomposed (from 5% to 95% weight loss) within 25° C. The thermal decomposition data clearly suggests the possibility of delivering a higher $T_g$ version of PPC in this invention with limited effect on the polymer decomposition in the presence of a photochemically or thermally active additive.

Prior solutions addressed residue concerns by identifying the root causes as decomposition products of the photoacid generators, namely iodine from the iodonium salts or metal species from antimony-containing anions, although a true resolution remains to be found. None of the photoactive additives in this invention contains heavy metal ions. Furthermore, the photobase generators PT-393 and PT-407M are not simple substitutes of existing photoacid generators. Unlike traditional PAGs which rely on the iodonium cations or fluorinated anions to generate a superacid, these photobase generators contain only carbon, hydrogen, nitrogen, and oxygen. Here the bases released are sufficiently strong to initiate base-catalyzed polycarbonate decomposition. This is a sharp contrast to the class of non-halogenated PAGs, which are generally ineffective in initiating polymer decomposition. Thus, the introduction of this class of photobase generators as the photo package addresses a long-standing desire of the semiconductor industry to remove halogenated components from patternable packaging or device fabrication materials.

This invention is further illustrated by the following examples which are provided for illustration purposes and in no way limit the scope of the present invention.

EXAMPLES

The following examples describe the procedures used for the preparation of various starting materials employed in the preparation of the compounds of this invention.

Alternating copolymerization of carbon dioxide ($CO_2$) and exo-epoxynorbornane (exo-NBaneOx) was carried out using (R,R), (S,S) or rac-(salcy)CoBzF$_5$ as a catalyst and PPNCl as a co-catalyst (Scheme).

Alternating copolymerization of $CO_2$ and propylene oxide (PO) was performed with (R,R) and (S,S)-(salcy)CoOBzF$_5$ to ascertain the activity of the catalysts before the copolymerization of $CO_2$ and exo-NBaneOx. The targeted number average molecular weight was 40,000.

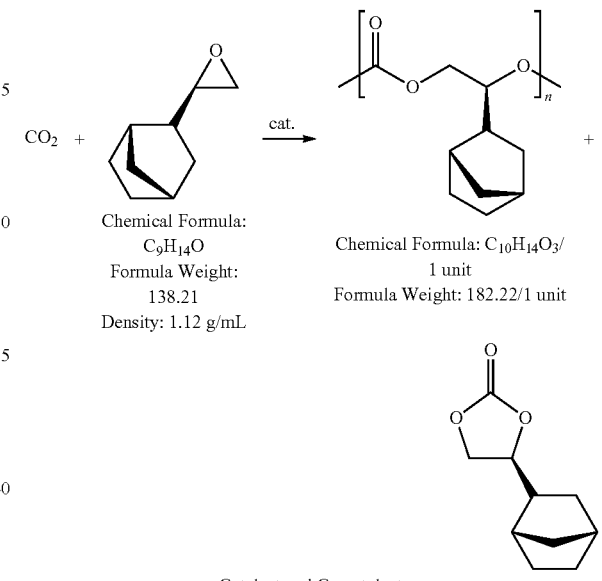

Copolymerization of CO2 and exo-Epoxyethylnorbornane.

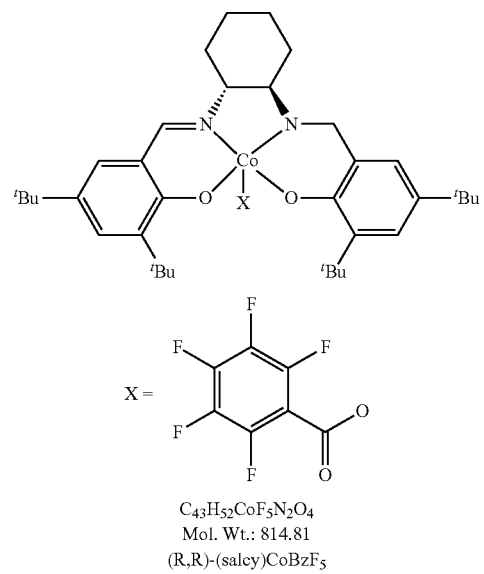

Catalyst and Co-catalyst

-continued

[structure: (PPN)Cl - bis(triphenylphosphine)iminium chloride]

$C_{36}H_{30}ClNP_2$
Mol. Wt.: 574.03
(PPN)Cl

General Methods exo-NBaneOx was degassed by sonication under vacuum then kept under nitrogen atmosphere. This process was repeated four times before polymerization. PO was vacuum distilled over calcium hydride after treating with potassium hydroxide to remove propionaldehyde by dimerization. (R,R) and (S,S)-(salcy)CoOBzF$_5$ were synthesized from commercially available corresponding Co(II) complexes. Those catalysts were used after confirmation of the activity by copolymerization of $CO_2$ and PO.

Analytical Methods $^1$H-NMR spectra were obtained in deuterated chloroform with tetramethylsilane (0.0 ppm) as an internal standard at 20° C. using a Bruker-DPX400 (400 MHz) spectrometer. Size exclusion chromatography was performed in tetrahydrofuran on a TSKgel Super MultiporeHZ-N size exclusion column at 40° C. using a Tosoh HLC-8220 system calibrated with polystyrene standards.

Comparative Example 1

Alternating Copolymerization of $CO_2$ and PO (to Test Activity)

A magnetic stirring bar, (R,R) (or (S,S))-(salcy)CoOBzF$_5$ (11.7 mg, 0.0143 mmol) and PPNCl (8.2 mg, 0.014 mmol) were placed in a stainless autoclave and the autoclave was sealed under nitrogen atmosphere. Rac-PO (2 mL, 28.6 mmol) was added to the autoclave via glass syringe, and then $CO_2$ was pressurized into the autoclave at 1.4 MPa. The $CO_2$ pressure was released after one hour stirring in a water bath at 22° C. This reaction mixture was analyzed by means of $^1$H-NMR and SEC (Table 1).

Following $^1$H-NMR peaks were used to calculate a monomer conversion and a product ratio (polycarbonate:cyclic carbonate).

Tertiary proton (1H) in PO—3.0 ppm
Tertiary proton (1H) in poly(propylene carbonate) (PPC)—5.0 ppm
Tertiary proton (1H) in propylene carbonate (cyclic carbonate, PC)—4.8 ppm Monomer conversion (%) =

$$\left\{1 - \frac{\text{peak integral at 3.0 ppm}}{\text{sum of peak integrals at 3.0, 4.8, 5.0 ppm}}\right\} * 100$$

PPC:PC = (peak integral at 5.0 ppm):(peak integral at 4.8 ppm)

Number average molecular weight ($M_n$) and poly dispersity ($M_w/M_n$) was obtained by SEC in relative to polystyrene standards.

TABLE 1

| run | cat. | conv. (%) | PPC:PC | $M_n$ (gmol$^{-1}$) | $M_w/M_n$ |
|---|---|---|---|---|---|
| 1 | (R,R)-(salcy)CoOBzF$_5$ | 46 | 91:9 | 14 500 | 1.16 |
| 2 | (S,S)-(salcy)CoOBzF$_5$ | 42 | 93:7 | 12 900 | 1.12 |

It was concluded that both the catalysts had the same level of activities.

Alternating Copolymerization of $CO_2$ and Exo-NBaneOx

Monomer conversion was calculated based on the $^1$H-NMR peaks listed below.

Epoxide 2Hs in the monomer—2.8-2.6 ppm
2Hs in norbornanyl group in the monomer and the products—2.4-2.0 ppm Monomer conversion (%) =

$$\left\{1 - \frac{\text{peak integral at 2.8 to 2.6 ppm}}{\text{sum of peak integrals at 2.4 to 2.0 ppm}}\right\} * 100$$

Product ratio of polycarbonate and cyclic carbonate was not able to calculate because of overlapping peaks.

Example 1

The polymerization was conducted with no solvent at the beginning. Dichloromethane was added after the reaction mixture solidified.

A magnetic stirring bar, (R,R)-(salcy)CoOBzF$_5$ (13.2 mg, 0.0162 mmol) and PPNCl (9.3 mg, 0.0162 mmol) were placed in an appropriately sized stainless autoclave and the autoclave was sealed under nitrogen atmosphere. exo-NBaneOx (4.0 mL, 32.4 mmol) was added to the autoclave via glass syringe, and then $CO_2$ was pressurized into the autoclave at 1.3 MPa and the mixture was stirred in a 22° C. water bath. Small amount samples were taken out by a syringe and needle after depressurized the autoclave for monomer conversion and molecular weight measurement (table 2). The reaction mixture was found solid at day 5. Dichloromethane (40 mL) was added at day 7 to dissolve the solidified reaction mixture. The reaction was stopped by releasing $CO_2$ at day 13, and the reaction solution was transferred to an appropriate size flask. The solvent was stripped by rotary evaporator. Chloroform was added to the resulting viscous liquid to become 40 mL total. To the chloroform solution was added hydrochloric acid 5% methanol solution and the solution turned to green. This greenish solution was stirred for 30 minutes and the solution was poured in a stirred methanol (250 mL) to obtain white solids. The precipitated solid was collected by filtration and dried under vacuum to afford white solid of 3.68 g (62.3% yield, $M_n$=19,600, $M_w/M_n$=1.14).

The reaction did not achieve the targeted molecular weight 40,000. The product was used as macro-initiator to obtain a higher molecular weight sample.

Example 2

A sample from Example 1 was used as macro-initiator. The reaction was conducted without solvents.

A magnetic stirring bar, (R,R)-(salcy)CoOBzF$_5$ (13.2 mg, 0.0162 mmol) and PPNCl (9.3 mg, 0.0162 mmol), RA134 (3.55 g) were placed in an appropriately sized stainless autoclave and the autoclave was sealed under nitrogen atmosphere. exo-NBaneOx (4.0 mL, 32.4 mmol) was added to the autoclave via glass syringe, and then CO$_2$ was pressurized into the autoclave at 1.3 MPa and the mixture was stirred in a 22° C. water bath. Small amount samples were taken out at day 2, 4, and 14 for GPC measurement (table 2). The reaction was stopped by releasing CO$_2$ at day 18, and a brown viscous liquid was transferred to a beaker and chloroform was then added to the liquid to be 80 mL. The solution turned green after an addition of 20 mL of hydrochloric acid 5% methanol solution. This greenish solution was stirred for 10 minutes and the solvents were stripped by rotary evaporator to reduce the volume to about 50 mL. The concentrated solution was poured in to 300 mL of methanol with stirring to precipitate the polymer. The white precipitate was collected by filtration and the solid was dried under vacuum. White polymeric material of 3.37 g was obtained ($M_n$=18,900, $M_w/M_n$=1.12).

Molecular weight was decreasing and polydispersity index was getting wider as the reaction time prolonged. The targeted molecular weight 40,000 was not achieved.

Examples 3-6

Four batches of polymers were combined to precipitate since the four reactions gave similar molecular weights.

Example 3

A magnetic stirring bar, (R,R)-(salcy)CoOBzF$_5$ (6.6 mg, 0.0081 mmol), (S,S)-(salcy)CoOBzF$_5$ (6.6 mg, 0.0081 mmol) and PPNCl (9.3 mg, 0.0162 mmol) were placed in an appropriately sized stainless autoclave and the autoclave was sealed under nitrogen atmosphere. exo-NBaneOx (4 mL, 32.4 mmol) was added to the autoclave via glass syringe, and then CO$_2$ was pressurized into the autoclave at 1.3 MPa and the mixture was stirred in a 22° C. water bath. A small amount of sample was taken out for $^1$H-NMR and GPC measurement at day 6 (table 2). After the sampling, exo-NBaneOx (4 mL, 32.4 mmol) was added and the autoclave was pressurized at 1.3 MPa with CO$_2$. The reaction was stopped by releasing CO$_2$ at day 7, and a brown viscous liquid was transferred to a beaker and chloroform was then added to the liquid to be 100 mL. The solution turned green after an addition of 20 mL of hydrochloric acid 5% methanol solution. This greenish solution was stirred for 30 minutes.

Example 4

A magnetic stirring bar, (R,R)-(salcy)CoOBzF$_5$ (13.2 mg, 0.0162 mmol), and PPNCl (9.3 mg, 0.0162 mmol) were placed in an appropriately sized stainless autoclave and the autoclave was sealed under nitrogen atmosphere. exo-NBaneOx (4.0 mL, 32.4 mmol) was added to the autoclave via glass syringe, and then CO$_2$ was pressurized into the autoclave at 1.3 MPa and the mixture was stirred in a 22° C. water bath. A small amount of sample was taken out for $^1$H-NMR and GPC measurement at day 6 (table 2). After the sampling, exo-NBaneOx (4 mL, 32.4 mmol) was added and the autoclave was pressurized at 1.3 MPa with CO$_2$. The reaction was stopped by releasing CO$_2$ at day 7, and a brown viscous liquid was transferred to a beaker and chloroform was then added to the liquid to be 100 mL. The solution turned green after an addition of 20 mL of hydrochloric acid 5% methanol solution. This greenish solution was stirred for 30 minutes. The solution Example 3 was added to this solution, and then the combined solutions were stripped down to be 50 mL by a rotary evaporator. The concentrated solution was poured into 350 mL of methanol upon stirring afforded a biscuit color precipitate. The precipitate was collected by filtration.

Example 5

A magnetic stirring bar, (R,R)-(salcy)CoOBzF$_5$ (13.2 mg, 0.0162 mmol), (S,S)-(salcy)CoOBzF$_5$ (13.2 mg, 0.0162 mmol) and PPNCl (18.9 mg, 0.0329 mmol) were placed in an appropriately sized stainless autoclave and the autoclave was sealed under nitrogen atmosphere. exo-NBaneOx (8.0 mL, 64.8 mmol) was added to the autoclave via glass syringe, and then CO$_2$ was pressurized into the autoclave at 1.3 MPa and the mixture was stirred at room temperature. A small amount of sample was taken out for $^1$H-NMR and GPC measurement at day 2 and 4 (table 2). After the sampling at day 2, exo-NBaneOx (4 mL, 32.4 mmol) was added. The reaction was stopped by releasing CO$_2$ at day 7 and the obtained solids were isolated.

Example 6

A magnetic stirring bar, (R,R)-(salcy)CoOBzF$_5$ (12.9 mg, 0.0158 mmol), (S,S)-(salcy)CoOBzF$_5$ (13 mg, 0.0160 mmol) and PPNCl (18.7 mg, 0.0326 mmol) were placed in an appropriately sized stainless autoclave and the autoclave was sealed under nitrogen atmosphere. exo-NBaneOx (8 mL, 64.8 mmol) was added to the autoclave via glass syringe, and then CO$_2$ was pressurized into the autoclave at 1.3 MPa and the mixture was stirred at room temperature. A small amount of sample was taken out for $^1$H-NMR and GPC measurement at day 2 and 4 (table 2). After the sampling, the autoclave was pressurized at 1.3 MPa with CO$_2$. The reaction was stopped by releasing CO$_2$ at day 7, and the reaction mixture was transferred to a beaker. The solids obtained from Example 5 were added and the total volume was adjusted to be 250 mL with chloroform. The solution turned green after an addition of 80 mL of hydrochloric acid 5% methanol solution. This greenish solution was stirred for 10 minutes and the solution formed two layers. The bottom layer was poured into 1000 mL of methanol upon stirring to give white solids. The white solids were collected by filtration.

The solids from Example 2 and Example 4 were then combined and dissolved in 200 mL of chloroform. The solution was poured into 1800 mL of methanol upon stirring to give a white precipitate. The white precipitate was collected by filtration and dried under vacuum to afford a dry polymer (19.6 g, $M_n$=21,400, $M_w/M_n$=1.18).

Example 7

A magnetic stirring bar, (R,R)-(salcy)CoOBzF$_5$ (39.6 mg, 0.0453 mmol), (S,S)-(salcy)CoOBzF (39.5 mg, 0.0448 mmol) and PPNCl (55.8 mg, 0.0972 mmol) were placed in an appropriately sized stainless autoclave and the autoclave was sealed under nitrogen atmosphere. exo-NBaneOx (24 mL, 194 mmol) was added to the autoclave via glass syringe, and then $CO_2$ was pressurized into the autoclave at 1.3 MPa and the mixture was stirred at room temperature. A small amount of sample was taken out for $^1$H-NMR and GPC measurement at day 1 and 4 (table 2). After the sampling, the autoclave was pressurized at 1.3 MPa with $CO_2$. The reaction was stopped by releasing $CO_2$ at day 6, and the reaction mixture was transferred to a beaker and the total volume was adjusted to be 500 mL with chloroform. Hydrochloric acid 5% methanol solution of 120 mL was added to the solution and two layers were formed. The bottom layer (about 250 mL) was poured into 1500 mL of methanol upon stirring to give white solids. The white precipitate was collected by filtration and dried under vacuum to afford the dry polymer (15.9 g, $M_n$=17,600, $M_w/M_n$=1.16).

Table 2 summarizes the results obtained for various Examples described above and the polycarbonate products obtained therefrom. Specifically, the Table 2 lists steric configuration of the catalyst, amount of the epoxide employed, the ratio of the epoxide/catalyst/co-catalyst, reaction time, conversion, the molecular weight of the resulting polymer as determined by the GPC methods in accordance with the procedures described herein, the amount and the yield of the polymer formed. The Table 2 also lists the rate of conversion and the GPC data at various time intervals as listed.

TABLE 2

Copolymerization of $CO_2$ and exo-Epoxyethylnorbornane

| Ex. No. | Config. of cat. | Epoxide (mL) | Epoxide:cat:co-cat | Time (days) | Conv. (%) | $M_n$ | $M_w/M_n$ | Pdt. (g) | Yield (%) |
|---|---|---|---|---|---|---|---|---|---|
| 1 | (R,R) | 4 | 2000:1:1 | 2 | 58 | 15700 | 1.1 | | |
| | | | | 5 | | 18000 | 1.14 | | |
| | | | | 10 | 73 | 19600 | 1.14 | 3.7 | 62 |
| 2 | (R,R) | 4 | 2000:1:1 | 2 | | 19000 | 1.12 | | |
| | | | | 4 | | 19000 | 1.13 | | |
| | | | | 14 | | 17800 | 1.13 | | |
| | | | | 18 | | 18900 | 1.12 | 3.4 | 29 |
| 3 | rac | 8 | 4000:1:1 | 6 | 79 | 22700 | 1.4 | 20 | 37 |
| 4 | (R,R) | 8 | 4000:1:1 | 6 | 72 | 21400 | 1.12 | 20 | 37 |
| 5 | rac | 12 | 3000:1:1 | 2 | 37 | 10300 | 1.1 | | |
| | | | | 4 | 42 | 12900 | 1.17 | | |
| | | | | 7 | | 21500 | 1.15 | 20 | 37 |
| 6 | rac | 8 | 2000:1:1 | 2 | 38 | 10900 | 1.1 | | |
| | | | | 4 | 71 | 21000 | 1.15 | | |
| | | | | 7 | | 12600 | 1.46 | 20 | 37 |
| 7 | rac | 24 | 2000:1:1 | 4 | | 13900 | 1.12 | | |
| | | | | 6 | 40 | 17800 | 1.15 | | |
| | | | | | | 17600 | 1.16 | 16 | 45 |

It is surprising that introducing a stereospecific version of the same rigid norbornane structure leads to a profound improvement in the solubility of the polycarbonate in common process solvents. The higher solubility of the resulting polycarbonate, exo-PNBaneEC from exo-NBaneOx allows facile formulation of the photoactive additives (PAGs or PBGs) with the polymer base solution.

Formulation Examples

The following Examples demonstrate the utility of the polycarbonates in certain optoelectronic applications.

Examples 16 to 21 summarize the TGA data for exo-PNBaneEC formulated with either a photoacid generator or a photobase generator. For comparison, data with PPC were included in Examples 8 to 15. The film material was generated by spin-coating the formulation onto a silicon substrate followed by soft bake at 120° C./5 min. The decomposition temperature ($T_d$) is defined as the temperature at which 5% weight loss was observed as the temperature was increased at 10° C./min under nitrogen in a dynamic TGA analysis. $\Delta T$ is defined as the difference between the decomposition temperature of the UV-exposed material and the glass transition temperature ($T_g$). Unless otherwise stated, UV exposure was performed at 365 nm with an exposure dose of 2 $J/cm^2$.

| Example | Additives | Polymer | $T_d$ (° C.) (Exposed) | $T_d$-$T_g$ (° C.) | $\Delta T <$ 30° C. |
|---|---|---|---|---|---|
| 8 | Rhodorsil PI2074/CPTX | PPC | 125 | 85 | No |
| 9 | NIT | PPC | 137 | 97 | No |
| 10 | GSID-26-1 | PPC | 105 | 65 | No |
| 11 | PAG-290 | PPC | 105 | 65 | No |
| 12 | PT-393* | PPC | 145 | 105 | No |
| 13 | PT-393/THMP* | PPC | 85 | 45 | No |
| 14 | PT-407M | PPC | 179 | 139 | No |
| 15 | PT-407M/THMP | PPC | 157 | 117 | No |
| 16 | Rhodorsil PI2074/CPTX | exo-PNBaneEC | 140 | 40 | No |
| 17 | NIT | exo-PNBaneEC | 196 | 96 | No |
| 18 | GSID-26-1 | exo-PNBaneEC | 167 | 67 | No |
| 19 | PAG-290 | exo-PNBaneEC | 185 | 85 | No |

-continued

| Example | Additives | Polymer | $T_d$ (° C.) (Exposed) | $T_d$-$T_g$ (° C.) | $\Delta T <$ 30° C. |
|---|---|---|---|---|---|
| 20 | PT-393* | exo-PNBaneEC | 102 | 2 | Yes |
| 21 | PT-393/THMP* | exo-PNBaneEC | 119 | 19 | Yes |

*Broadband exposure applied for 15 min

As evident from the above table, exo-PNBaneEC with base generator PT-393 provided the lowest $\Delta T$ across all the examples, suggesting that the formulation will likely give rise to high resolution images with maximum retention of pattern fidelity.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I):

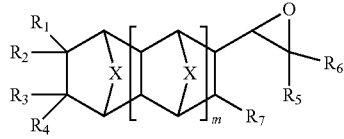

wherein:
m is an integer from 0 to 2, inclusive;
X is —CH$_2$— or —CH$_2$—CH$_2$—;
each occurrence of R$_1$, R$_2$, R$_3$ and R$_4$ independently represents hydrogen, ethyl, linear or branched C$_3$-C$_{12}$-alkyl, C$_3$-C$_{12}$-cycloalkyl, C$_6$-C$_{12}$-bicycloalkyl, C$_7$-C$_{14}$-tricycloalkyl, C$_{10}$-C$_{14}$-tetracycloalkyl, C$_6$-C$_{10}$-aryl, C$_6$-C$_{10}$-aryl-C$_1$-C$_3$-alkyl, C$_5$-C$_{10}$-heteroaryl, C$_5$-C$_{10}$-heteroaryl-C$_1$-C$_3$-alkyl, C$_1$-C$_{12}$-alkoxy, C$_3$-C$_{12}$-cycloalkoxy, C$_6$-C$_{12}$-bicycloalkoxy, C$_7$-C$_{14}$-tricycloalkoxy, C$_{10}$-C$_{14}$-tetracycloalkoxy, C$_6$-C$_{10}$-aryloxy-C$_1$-C$_3$-alkyl, C$_5$-C$_{10}$-heteroaryloxy-C$_1$-C$_3$-alkyl, C$_6$-C$_{10}$-aryloxy, C$_5$-C$_{10}$-heteroaryloxy, C$_1$-C$_6$-acyloxy and halogen; or
R$_1$ and R$_2$ or R$_2$ and R$_3$ or R$_3$ and R$_4$ taken together with the carbon atom to which they are attached form a C$_3$-C$_{12}$-cycloalkyl ring optionally containing one or more hetero atoms selected from nitrogen, oxygen and sulfur;
each occurrence of R$_5$ and R$_6$ independently represents hydrogen, methyl, ethyl, linear or branched C$_3$-C$_{12}$-alkyl; or
R$_5$ and R$_6$ taken together with the carbon atom to which they are attached form a C$_3$-C$_{12}$-cycloalkyl ring optionally containing one or more hetero atoms selected from nitrogen, oxygen and sulfur;
R$_7$ represents hydrogen, methyl, ethyl, linear or branched C$_3$-C$_{12}$-alkyl and phenyl;
or an enantiomer, stereoisomer or a racemic mixture thereof; and
with the exception of following compounds:
2-(bicyclo[2.2.1]heptan-2-yl)oxirane;
2-(6-phenylbicyclo[2.2.1]heptan-2-yl)oxirane; and
2-(5-phenylbicyclo[2.2.1]heptan-2-yl)oxirane.

2. The compound according to claim 1, wherein:
m is 0 or 1;
X is CH$_2$;
each occurrence of R$_1$, R$_2$, R$_3$ and R$_4$ independently represents hydrogen, cyclohexyl, bicyclo[2.2.1]heptanyl and decahydro-1,4:5,8-dimethanonaphthalenyl; and
each occurrence of R$_5$ and R$_6$ independently represents hydrogen, methyl and ethyl; and
R$_7$ is hydrogen.

3. The compound according to claim 1, which is selected from:
(S)-2-((1S,2S,4R)-bicyclo[2.2.1]heptan-2-yl)oxirane;
(R)-2-((1S,2S,4R)-bicyclo[2.2.1]heptan-2-yl)oxirane;
(S)-2-((1R,2R,4S)-bicyclo[2.2.1]heptan-2-yl)oxirane;
(R)-2-((1R,2R,4S)-bicyclo[2.2.1]heptan-2-yl)oxirane;
2-(6-cyclohexylbicyclo[2.2.1]heptan-2-yl)oxirane;
2-(5-cyclohexylbicyclo[2.2.1]heptan-2-yl)oxirane;
2-([2,2'-bi(bicyclo[2.2.1]heptan)]-6-yl)oxirane;
2-([2,2'-bi(bicyclo[2.2.1]heptan)]-5-yl)oxirane;
2-(6-(decahydro-1,4:5,8-dimethanonaphthalen-2-yl)bicyclo[2.2.1]heptan-2-yl)oxirane;
2-(5-(decahydro-1,4:5,8-dim ethanonaphthalen-2-yl)bicyclo[2.2.1]heptan-2-yl)oxirane; and
2-(decahydro-1,4:5,8-dimethanonaphthalen-2-yl)oxirane.

4. A polymer comprising the repeat units of formula (III), said repeat unit is derived from a compound of formula (I):

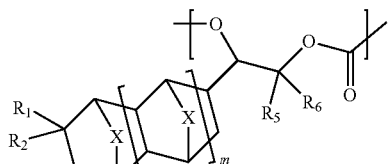

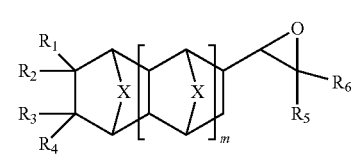

wherein:
in is an integer from 0 to 2, inclusive;
X is —CH$_2$— or —CH$_2$—CH$_2$—;
each occurrence of R$_1$, R$_2$, R$_3$ and R$_4$ independently represents hydrogen, ethyl, linear or branched C$_3$-C$_{12}$-alkyl, C$_3$-C$_{12}$-cycloalkyl, C$_6$-C$_{12}$-bicycloalkyl, C$_7$-C$_{14}$-tricycloalkyl, C$_{10}$-C$_{14}$-tetracycloalkyl, C$_6$-C$_{10}$-aryl, C$_6$-C$_{10}$-aryl-C$_1$-C$_3$-alkyl, C$_5$-C$_{10}$-heteroaryl, C$_5$-C$_{10}$-heteroaryl-C$_1$-C$_3$-alkyl, C$_1$-C$_{12}$-alkoxy, C$_3$-C$_{12}$-cycloalkoxy, C$_6$-C$_{12}$-bicycloalkoxy, C$_7$-C$_{14}$-tricycloalkoxy, C$_{10}$-C$_{14}$-tetracycloalkoxy, C$_6$-C$_{10}$-aryloxy-C$_1$-C$_3$-alkyl, C$_5$-C$_{10}$-heteroaryloxy-C$_1$-C$_3$-alkyl, C$_6$-C$_{10}$-aryloxy, C$_5$-C$_{10}$-heteroaryloxy, C$_1$-C$_6$-acyloxy and halogen; or
R$_1$ and R$_2$ or R$_2$ and R$_3$ or R$_3$ and R$_4$ taken together with the carbon atom to which they are attached form a C$_3$-C$_{12}$-cycloalkyl ring optionally containing one or more hetero atoms selected from nitrogen, oxygen and sulfur; and
each occurrence of R$_5$ and R$_6$ independently represents hydrogen, methyl, ethyl, linear or branched C$_3$-C$_{12}$-alkyl; or
R$_5$ and R$_6$ taken together with the carbon atom to which they are attached form a C$_3$-C$_{12}$-cycloalkyl ring optionally containing one or more hetero atoms selected from nitrogen, oxygen and sulfur.

5. The polymer according to claim 4, wherein:
m is 0 or 1;
X is CH$_2$;
each occurrence of R$_1$, R$_2$, R$_3$ and R$_4$ independently represents hydrogen, phenyl, cyclohexyl, bicyclo[2.2.1]heptanyl and decahydro-1,4:5,8-dimethanonaphthalenyl; and
each occurrence of R$_5$ and R$_6$ independently represents hydrogen, methyl and ethyl.

6. The polymer according to claim 4, wherein said repeat unit is derived from a compound selected from one or more of the following:
2-(bicyclo[2.2.1]heptan-2-yl)oxirane;
2-(bicyclo[2.2.1]heptan-2-yl)oxirane;
2-(6-phenylbicyclo[2.2.1]heptan-2-yl)oxirane;

2-(5-phenylbicyclo[2.2.1]heptan-2-yl)oxirane;
(S)-2-((1S,2S,4R)-bicyclo[2.2.1]heptan-2-yl)oxirane;
(R)-2-((1S,2S,4R)-bicyclo[2.2.1]heptan-2-yl)oxirane;
(S)-2-((1R,2R,4S)-bicyclo[2.2.1]heptan-2-yl)oxirane;
(R)-2-((1R,2R,4S)-bicyclo[2.2.1]heptan-2-yl)oxirane;
2-(6-cyclohexylbicyclo[2.2.1]heptan-2-yl)oxirane;
2-(5-cyclohexylbicyclo[2.2.1]heptan-2-yl)oxirane;
2-([2,2'-bi(bicyclo[2.2.1]heptan)]-6-yl)oxirane;
2-([2,2'-bi(bicyclo[2.2.1]heptan)]-5-yl)oxirane;
2-(6-(decahydro-1,4:5,8-dimethanonaphthalen-2-yl)bicyclo[2.2.1]heptan-2-yl)oxirane;
2-(5-(decahydro-1,4:5,8-dimethanonaphthalen-2-yl)bicyclo[2.2.1]heptan-2-yl)oxirane; and
2-(decahydro-1,4:5,8-dimethanonaphthalen-2-yl)oxirane.

7. The polymer according to claim 4, wherein the weight average molecular weight of said polymer is from about 1,000 to about 300,000.

8. The polymer according to claim 4, wherein said polymer exhibits a glass transition temperature of at least about 60° C.

9. The polymer according to claim 4, wherein said polymer exhibits a glass transition temperature of at least about 100° C.

10. A process for making a polymer of formula (III) according to claim 4 comprising:
reacting a compound of formula (I) with carbon dioxide in the presence of a ligand-supported metal catalyst:

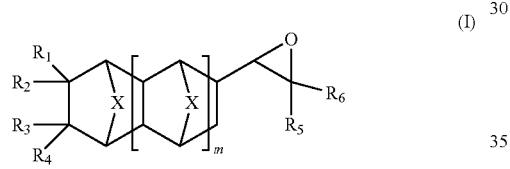

(I)

wherein:
m is an integer from 0 to 2, inclusive;
X is —$CH_2$— or —$CH_2$—$CH_2$—;
each occurrence of $R_1$, $R_2$, $R_3$ and $R_4$ independently represents hydrogen, ethyl, linear or branched $C_3$-$C_{12}$-alkyl, $C_3$-$C_{12}$-cycloalkyl, $C_6$-$C_{12}$-bicycloalkyl, $C_7$-$C_{14}$-tricycloalkyl, $C_{10}$-$C_{14}$-tetracycloalkyl, $C_6$-$C_{10}$-aryl, $C_6$-$C_{10}$-aryl-$C_1$-$C_3$-alkyl, $C_5$-$C_{10}$-heteroaryl, $C_5$-$C_{10}$-heteroaryl-$C_1$-$C_3$-alkyl, $C_1$-$C_{12}$-alkoxy, $C_3$-$C_{12}$-cycloalkoxy, $C_6$-$C_{12}$-bicycloalkoxy, $C_7$-$C_{14}$-tricycloalkoxy, $C_{10}$-$C_{14}$-tetracycloalkoxy, $C_6$-$C_{10}$-aryloxy-$C_1$-$C_3$-alkyl, $C_5$-$C_{10}$-heteroaryloxy-$C_1$-$C_3$-alkyl, $C_6$-$C_{10}$-aryloxy, $C_5$-$C_{10}$-heteroaryloxy, $C_1$-$C_6$-acyloxy and halogen;
$R_1$ and $R_2$ or $R_2$ and $R_3$ or $R_3$ and $R_4$ taken together with the carbon atom to which they are attached form a $C_3$-$C_{12}$-cycloalkyl ring optionally containing one or more hetero atoms selected from nitrogen, oxygen and sulfur; and
each occurrence of $R_5$ and $R_6$ independently represents hydrogen, methyl, ethyl, linear or branched $C_3$-$C_{12}$-alkyl; or
$R_5$ and $R_6$ taken together with the carbon atom to which they are attached form a $C_3$-$C_{12}$-cycloalkyl ring optionally containing one or more hetero atoms selected from nitrogen, oxygen and sulfur.

11. The process according to claim 10 which includes a halogenated solvent.

12. The process according to claim 10, wherein the ligand-supported metal catalyst is selected from the group consisting of chromium, manganese, iron, cobalt, nickel, ruthenium, rhodium, palladium, iridium, platinum and zinc.

13. The process according to claim 10, wherein the catalyst is a cobalt metal complex of formulae (IV) or (V):

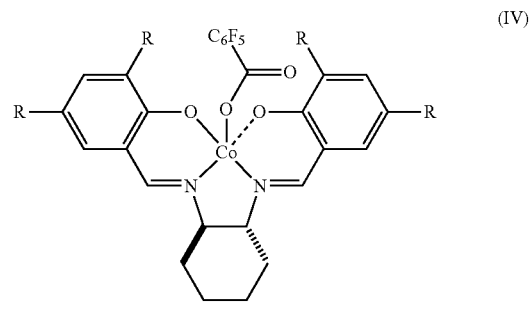

(IV)

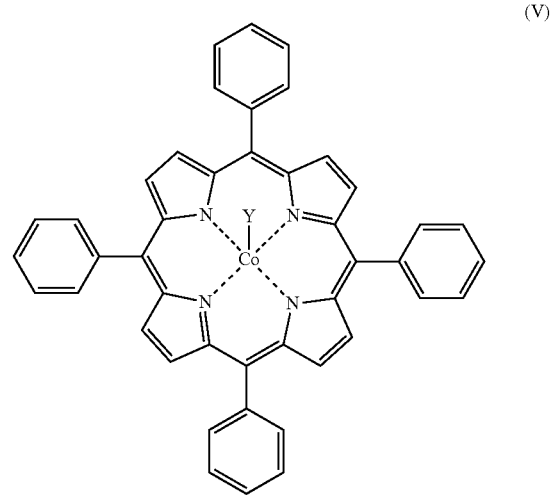

(V)

wherein
R is methyl, ethyl, linear or branched $C_3$-$C_{12}$-alkyl, $C_3$-$C_{12}$-cycloalkyl and $C_6$-$C_{10}$-aryl; and
Y is halogen, acetate, trifluoroacetate, benzoate, tosylate, triflate, mesylate, $C_6F_5CO_2$ and azide.

14. The process according to claim 13, wherein R is tert-butyl and Y is chlorine.

15. The process according to claim 10, wherein it further comprises a co-catalyst of the formula (VI):

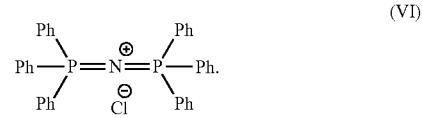 [SMILES: c1ccc(P(=[N+]=P(c2ccccc2)(c2ccccc2)c2ccccc2)(c2ccccc2)c2ccccc2)cc1 ; [Cl-]]

(VI)

16. A sacrificial polymer composition comprising:
a polymer according to claim 4;
a photoacid generator (PAG) or photobase generator (PBG) or mixtures thereof; and
a solvent.

17. The sacrificial polymer composition according to claim 16, which further comprises a thermally activated acid generator (TAG).

18. The sacrificial polymer composition of claim 16 where the solvent is selected from anisole, n-butyl acetate (BuOAc), dimethylacetamide (DMAc), cyclopentanone, cyclohexanone, gamma butyrolactone (GBL), propyleneglycol-monomethylether acetate (PGMEA) and mixtures thereof.

19. The sacrificial polymer composition of claim 16 where the photoacid or photobase generator is selected from the following:

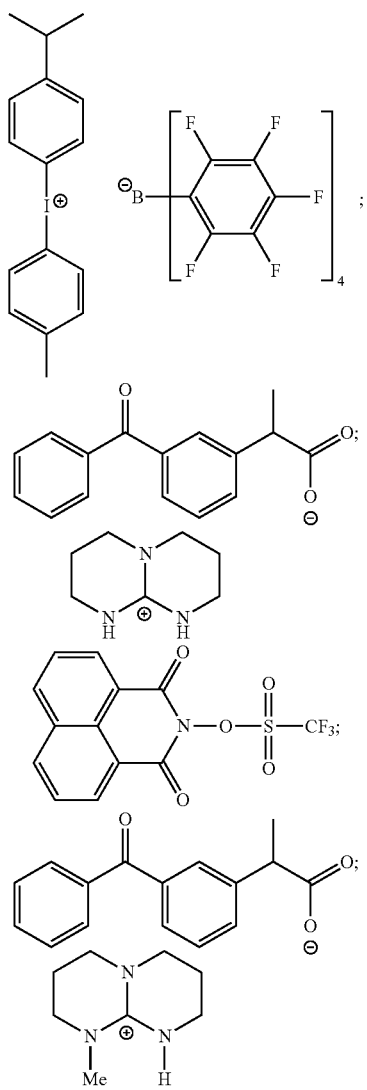

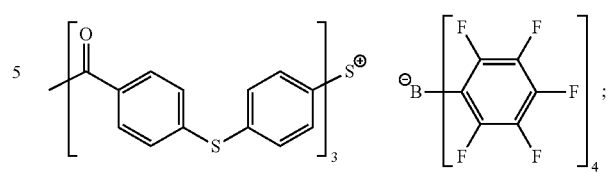

and mixtures in any combination thereof.

20. The sacrificial polymer composition of claim 16, which further comprises optional additives selected from the group consisting of sensitizers, adhesion promoters, antioxidants, antioxidant synergists and fillers.

21. The sacrificial polymer composition of claim 20, where said optional additives are selected from 1-chloro-4-propylthioxanthane (CPTX), isopropyl thioxanthone (ITX), phenothiazine, benzoquinone and 1,1,1-tris(hydroxymethyl) propane (THMP).

22. The sacrificial polymer composition of claim 16 where the photoacid generator (PAG) or photobase generator loading is from 0.15 parts per hundred polymer to 10 parts per hundred polymer, inclusive.

23. The sacrificial polymer composition of claim 16 where the difference between the thermal decomposition temperature of the polymer ($T_d$) after actinic radiation in said composition and the glass transition temperature of the polymer ($T_g$) is not greater than 30° C.

24. The sacrificial polymer composition of claim 20 where the difference between the thermal decomposition temperature of the polymer ($T_d$) after actinic radiation in said composition and the glass transition temperature of the polymer ($T_g$) is not greater than 30° C.

* * * * *